US012584131B2

(12) United States Patent (10) Patent No.: US 12,584,131 B2
Grompe et al. (45) Date of Patent: Mar. 24, 2026

(54) METHODS OF GENE THERAPY

(71) Applicant: OREGON HEALTH & SCIENCE UNIVERSITY, Portland, OR (US)

(72) Inventors: Markus Grompe, Portland, OR (US); Amita Tiyaboonchai, Portland, OR (US)

(73) Assignee: OREGON HEALTH & SCIENCE UNIVERSITY, Portland, OR (US)

( * ) Notice: Subject to any disclaimer, the term of this patent is extended or adjusted under 35 U.S.C. 154(b) by 1203 days.

(21) Appl. No.: 17/045,806

(22) PCT Filed: Apr. 30, 2019

(86) PCT No.: PCT/US2019/029890
§ 371 (c)(1),
(2) Date: Oct. 7, 2020

(87) PCT Pub. No.: WO2019/213065
PCT Pub. Date: Nov. 7, 2019

(65) Prior Publication Data
US 2021/0130832 A1 May 6, 2021

Related U.S. Application Data

(60) Provisional application No. 62/664,932, filed on Apr. 30, 2018, provisional application No. 62/664,930, filed on Apr. 30, 2018.

(51) Int. Cl.
*C12N 15/113* (2010.01)
*A61K 31/167* (2006.01)
*C12N 9/22* (2006.01)
*C12N 15/86* (2006.01)

(52) U.S. Cl.
CPC ........ *C12N 15/1137* (2013.01); *A61K 31/167* (2013.01); *C12N 9/22* (2013.01); *C12N 15/86* (2013.01); *C12N 2310/14* (2013.01); *C12N 2310/531* (2013.01); *C12N 2750/14141* (2013.01)

(58) Field of Classification Search
None
See application file for complete search history.

(56) References Cited

U.S. PATENT DOCUMENTS

| | | | | |
|---|---|---|---|---|
| 5,980,886 A | * | 11/1999 | Kay | A61K 48/00 |
| | | | | 424/93.1 |
| 2005/0005312 A1 | * | 1/2005 | Wu | A01K 67/0271 |
| | | | | 800/9 |
| 2009/0181910 A1 | | 7/2009 | Chow et al. | |
| 2009/0265795 A1 | | 10/2009 | Baldwin | |

| | | | | |
|---|---|---|---|---|
| 2011/0035816 A1 | | 2/2011 | Ostertag et al. | |
| 2013/0316391 A1 | * | 11/2013 | Bourner | G01N 33/5035 |
| | | | | 435/366 |
| 2014/0179770 A1 | * | 6/2014 | Zhang | A61P 19/08 |
| | | | | 435/320.1 |

FOREIGN PATENT DOCUMENTS

| | | | | |
|---|---|---|---|---|
| WO | WO-0040271 A2 | * | 7/2000 | ........... A61K 31/167 |
| WO | 2015/089462 A1 | | 6/2015 | |
| WO | WO-2015153940 A1 | * | 10/2015 | ........... C12N 15/111 |

OTHER PUBLICATIONS

Lee, William M. "Acetaminophen: Pathology and Clinical Presentation of Hepatotoxicity." In Drug-Induced Liver Disease, edited by Neil Kaplowitz, pp. 389-405. New York: Informa Healthcare, USA, 2007.*

Fontana et al. Drug-Induced Liver Injury Network (DILIN) Prospective Study. Rationale, Design and Conduct. Drug Safety, 2009. 32 (1):55-69.*

Jang, et al., "Hepatoprotective effect of baicalin, a major flavone from Scutellaria radix, on acetaminophen-induced liver injury in mice" Immunopharmacol Immunotoxicol. (2003) 25(4):585-94.

Wang, et al., "Hepato-protective effect of resveratrol against acetaminophen-induced liver injury is associated with inhibition of CYP-mediated bioactivation and regulation of SIRT1-p53 signaling pathways" Toxicol Lett. (2015) 236 (2):82-9.

Francis, et al., "A patent review on the development of human cytochrome P450 inhibitors" Expert Opin Ther Pat. (2014) 24(6):699-717.

Lu, et al., "CRISPR knockout rat cytochrome P450 3A1/2 model for advancing drug metabolism and pharmacokinetics research" Sci Rep. (2017) 7:4292.

Nygaard, et al., "A universal system to select gene-modified hepatocytes in vivo" Sci Transl Med. (2016) 8 (342):342ra79.

Nygaard, et al., "948. Efficient In Vivo Selection of GeneTargeted Hepatocytes Using AcetaminophenInduced Liver Toxicity" Molecular Therapy (2018) 26(5S1):431.

Chen, et al., "Small Interfering RNA-Mediated Silencing of Cytochrome P450 3A4 Gene" Drug Metab. Dispos. (2006) 34(9):1650-7.

Lee, et al., "Role of CYP2E1 in the hepatotoxicity of acetaminophen" J. Biol. Chem. (1996) 271(20):12063-7.

Henderson, et al., "Inactivation of the hepatic cytochrome P450 system by conditional deletion of hepatic cytochrome P450 reductase" J. Biol. Chem. (2003) 278(15):13480-6.

Vonada, et al., "Therapeutic liver repopulation by transient acetaminophen selection of gene-modified hepatocytes" Sci. Transl. Med. (2021) 13(597): doi:10.1126/scitranslmed.abg3047, pp. 1-18.

* cited by examiner

*Primary Examiner* — Christopher M Babic
*Assistant Examiner* — Kimberly A Aron
(74) *Attorney, Agent, or Firm* — Robert C. Netter, Jr.; Dann, Dorfman, Herrell & Skillman

(57) ABSTRACT

Compositions and methods for gene and/or cell editing are provided.

46 Claims, 11 Drawing Sheets
Specification includes a Sequence Listing.

Drug-sensitive hepatocyte

Drug-resistant hepatocyte

Cell death

Cell expansion

Weeks of Acetaminophen Treatment

SEQUENCE LISTING

<160> NUMBER OF SEQ ID NOS: 523

<210> SEQ ID NO 1
<211> LENGTH: 7889
<212> TYPE: DNA
<213> ORGANISM: Artificial Sequence
<220> FEATURE:
<223> OTHER INFORMATION: Cypor human factor 9 gene ride

<400> SEQUENCE: 1

```
ttggccactc cctctctgcg cgctcgctcg ctcactgagg ccgggcgacc aaaggtcgcc      60
cgacgcccgg gctttgcccg ggcggcctca gtgagcgagc gagcgcgcag agagggagtg     120
gccaactcca tcactagggg ttcctggagg ggtggagtcg tgacgtaaag atctgatatc     180
atcgatcgcg atgcattaat taagcggccg ctgtacatag gaggttcgaa ccctgctgaa     240
gggagaggtt ccaatactac aaaatgtagc gggatattgt catcaccttt ggggacatgt     300
catcatggtc cccagacaga gttacaaaac tcatcccta cacagcacta tgtctctggt     360
actgtttgtt ctacagatgt caacaacaga ggcccagcca tctcctattg cttggcttgt     420
cagtctttct agcctcccca ttattaattt caaatggggc aggtgttagg agggcaaaaa     480
tccacatatt aagtgcaaag cctttcagga gatttcctga aactagacaa aacccgtgtg     540
actggcatcg attattctat ttgatctagc tagtcctagc aaagtgacaa ctgctactcc     600
cctcctacac agccaagatt cctaagttgg cagtggcatg cttaatcctc aaagccaaag     660
ttacttggct ccaagattta tagccttaaa ctgtggcctc acattccttc ctatcttact     720
ttcctgcact ggggtaaatg tctccttgct cttcttgctt tctgtcctac tgcagggctc     780
ttgctgagct ggtgaagcac aagcccaagg ctacagcgga gcaactgaag actgtcatgg     840
atgactttgc acagttcctg gatacatgtt gcaaggctgc tgacaaggac acctgcttct     900
cgactgaggt cagaaacgtt tttgcatttt gacgatgttc agtttccatt ttctgtgcac     960
gtggtcaggt gtagctctct ggaactcaca cactgaataa ctccaccaat ctagatgttg    1020
ttctctacgt aactgtaata gaaactgact tacgtagctt ttaatttta ttttctgcca    1080
```

-continued

```
cactgctgcc tattaaatac ctattatcac tatttggttt caaatttgtg acacagaaga    1140
gcatagttag aaatacttgc aaagcctaga atcatgaact catttaaacc ttgccctgaa    1200
atgtttcttt ttgaattgag ttattttaca catgaatgga cagttaccat tatatatctg    1260
aatcatttca cattccctcc catggcctaa caacagttta tcttcttatt ttgggcacaa    1320
cagatgtcag agagcctgct ttaggaattc taagtagaac tgtaattaag caatgcaagg    1380
cacgtacgtt tactatgtca ttgcctatgg ctatgaagtg caaatcctaa cagtcctgct    1440
aatacttttc taacatccat catttctttg ttttcagggt ccaaaccttg tcactagatg    1500
caaagacgcc ttagccggaa gcggcgccac caatttcagc ctgctgaaac aggccggcga    1560
cgtggaagag aaccctggcc ctgctagcca gcgcgtgaac atgattatgg ccgagagccc    1620
tggcctgatc accatctgcc tgctgggcta cctgctgagc gccgagtgta ccgtgttcct    1680
ggaccacgag aacgccaaca agatcctgaa cagacccaag agatacaaca gcggcaagct    1740
ggaagagttc gtgcagggca acctggaacg cgagtgcatg gaagagaagt gcagcttcga    1800
agaggccaga gaggtgttcg agaacaccga gagaaccacc gagttctgga agcagtacgt    1860
ggacggcgac cagtgcgaga gcaacccttg tctgaacggc ggcagctgca aggacgacat    1920
caacagctac gagtgctggt gcccccttcgg cttcgagggc aagaactgcg agctggacgt    1980
gacctgcaac atcaagaacg gcagatgcga gcagttctgc aagaacagcg ccgacaacaa    2040
ggtcgtgtgc tcctgcaccg agggctacag actggccgag aaccagaagt cctgcgagcc    2100
cgctgtgcct ttcccatgcg gaagagtgtc cgtgtcccag accagcaagc tgaccagagc    2160
cgagacagtg ttccccgacg tggactacgt gaacagcacc gaggccgaga caatcctgga    2220
caacatcacc cagagcaccc agtccttcaa cgacttcacc agagtcgtgg gcggcgagga    2280
tgctaagcct ggccagttcc cgtggcaggt ggtgctgaac ggaaaggtgg acgccttctg    2340
cggcggctcc atcgtgaacg agaagtggat cgtgacagcc gcccactgcg tggaaaccgg    2400
cgtgaagatc acagtggtgg ccggcgagca caacatcgag gaaaccgagc acacagagca    2460
gaaaagaaac gtgatcagga tcatccccca ccacaactac aacgccgcca tcaacaagta    2520
caaccacgat atcgccctgc tggaactgga cgagcccctg gtgctgaata gctacgtgac    2580
ccccatctgt atcgccgaca aagagtacac caacatcttt ctgaagttcg gcagcggcta    2640
cgtgtccggc tggggcagag tgtttcacaa gggcagatcc gctctggtgc tgcagtacct    2700
gagagtgcct ctggtggaca gagccacctg tctgagaagc accaagttca ccatctacaa    2760
caacatgttc tgcgctggct ccacgagggg cggcagagac tcttgtcagg gcgattctgg    2820
cggccctcac gtgacagagg tggaaggcac cagctttctg accggcatca tcagctgggg    2880
cgaggaatgc gccatgaagg ggaagtacgg catctacacc aaggtgtcca gatacgtgaa    2940
ctggatcaaa gaaaagacca agctgacata agctagctta gcctaaacac atcacaacca    3000
caaccttctc aggtaactaa ccggtccacg actgatgagt ccgtgaggac gaaacgagta    3060
agctcgtctc gtgggggtcc tgacctacgt tttagagcta gaaatagcaa gttaaaataa    3120
ggctagtccg ttatcaactt gaaaaagtgg caccgagtcg gtgcttttgg ccggcatggt    3180
cccagcctcc tcgctggcgc cggctgggca acatgcttcg gcatggcgaa tgggacctta    3240
agccactatg tggagtcctc catgttagcc tagtcaagct tatcctctgg atgaagttga    3300
aaccatatga aggaatattt ggggggtggg tcaaaacagt tgtgtatcaa tgattccatg    3360
tggtttgacc caatcattct gtgaatccat ttcaacagaa gatacaacgg gttctgtttc    3420
ataataagtg atccacttcc aaatttctga tgtgccccat gctaagcttt aacagaattt    3480
```

```
atcttcttat gacaaagcag cctcctttga aaatatagcc aactgcacac agctatgttg   3540
atcaattttg tttataatct tgcagaagag aatttttaa aatagggcaa taatggaagg   3600
ctttggcaaa aaaattgttt ctccatatga aaacaaaaaa cttattttt tattcaagca    3660 aagaacctat agacataagg ctatttcaaa attatttcag ttttagaaag aattgaaagt   3720
tttgtagcat tctgagaaga cagctttcat ttgtaatcat aggtaatatg taggtcctca   3780
gaaatggtga gacccctgac tttgacactt ggggactctg agggaccagt gatgaagagg   3840
gcacaactta tatcacacat gcacgagttg gggtgagagg gtgtcacaac atctatcagt   3900
gtgtcatctg cccaccaagt aacagatgtc agctaagact aggtcatgtg taggctgtct   3960
acaccagtga aaatcgcaaa aagaatctaa gaaattccac atttctagaa aataggtttg   4020
gaaaccgtat tccattttac aaaggacact tacatttctc tttttgtttt ccaggctacc   4080
ctgagaaaaa aagacatgaa gactcaggac tcatcttttc tgttggtgta aaatcaacac   4140
cctaaggaac acaaatttct ttaaacattt gacttcttgt ctctgtgctg caattaataa   4200
aaaatggaaa gaatctactc tgtggttcag aactctatct tccaaaggcg cgcttcaccc   4260
tagcagcctc tttggctcag aggaatccct gcctttcctc ccttcatctc agcagagaat   4320
gtagttccac atgggactag tgtacacgcg tgatatcaga tctgttacgt agataagtag   4380
catggcgggt taatcattaa ctacaaggaa cccctagtga tggagttggc cactccctct   4440
ctgcgcgctc gctcgctcac tgaggccgcc cgggcaaagc ccgggcgtcg ggcgaccttt   4500
ggtcgcccgg cctcagtgag cgagcgagcg cgcagagagg gagtggccaa agcgcgcagc   4560
tgcctgcagg tcgactctag aggatccccg ggtaccgagc tcgaattcac tggccgtcgt   4620
tttacaacgt cgtgactggg aaaaccctgg cgttacccaa cttaatcgcc ttgcagcaca   4680 tcccccttc gccagctggc gtaatagcga agaggcccgc accgatcgcc cttcccaaca    4740
gttgcgcagc ctgaatggcg aatggcgcct gatgcggtat tttctcctta cgcatctgtg   4800
cggtatttca caccgcatac gtcaaagcaa ccatagtacg cgccctgtag cggcgcatta   4860
agcgcggcgg gtgtggtggt tacgcgcagc gtgaccgcta cacttgccag cgcttagcgc   4920
ccgctccttt cgctttcttc ccttcctttc tcgccacgtt cgccggcttt ccccgtcaag   4980
ctctaaatcg ggggctccct ttagggttcc gatttagtgc tttacggcac ctcgacccca   5040
aaaaacttga tttgggtgat ggttcacgta gtgggccatc gccctgatag acggtttttc   5100
gccctttgac gttggagtcc acgttcttta atagtggact cttgttccaa actggaacaa   5160
cactcaactc tatctcgggc tattcttttg atttataagg gattttgccg atttcggtct   5220
attggttaaa aaatgagctg atttaacaaa aatttaacgc gaattttaac aaaatattaa   5280
cgtttacaat tttatggtgc actctcagta caatctgctc tgatgccgca tagttaagcc   5340
agccccgaca cccgccaaca cccgctgacg cgccctgacg ggcttgtctg ctcccggcat   5400
ccgcttacag acaagctgtg accgtctccg ggagctgcat gtgtcagagg ttttcaccgt   5460
catcaccgaa acgcgcgaga cgaaagggcc tcgtgatacg cctattttta taggttaatg   5520
tcatgataat aatggtttct tagacgtcag gtggcacttt tcggggaaat gtgcgcggaa   5580
cccctatttg tttattttc taaatacatt caaatatgta tccgctcatg agacaataac    5640
cctgataaat gcttcaataa tattgaaaaa ggaagagtat gagtattcaa catttccgtg   5700
tcgcccttat tcccttttt gcggcatttt gccttcctgt ttttgctcac ccagaaacgc    5760
tggtgaaagt aaaagatgct gaagatcagt tgggtgcacg agtgggttac atcgaactgg   5820
```

-continued

```
atctcaacag cggtaagatc cttgagagtt ttcgccccga agaacgtttt ccaatgatga    5880
gcacttttaa agttctgcta tgtggcgcgg tattatcccg tattgacgcc gggcaagagc    5940
aactcggtcg ccgcatacac tattctcaga atgacttggt tgagtactca ccagtcacag    6000
aaaagcatct tacggatggc atgacagtaa gagaattatg cagtgctgcc ataaccatga    6060
gtgataacac tgcggccaac ttacttctga caacgatcgg aggaccgaag gagctaaccg    6120
cttttttgca caacatgggg gatcatgtaa ctcgccttga tcgttgggaa ccggagctga    6180
atgaagccat accaaacgac gagcgtgaca ccacgatgcc tgtagcaatg gcaacaacgt    6240
tgcgcaaact attaactggc gaactactta ctctagcttc ccggcaacaa ttaatagact    6300
ggatggaggc ggataaagtt gcaggaccac ttctgcgctc ggcccttccg gctggctggt    6360
ttattgctga taaatctgga gccggtgagc gtgggtctcg cggtatcatt gcagcactgg    6420
ggccagatgg taagccctcc cgtatcgtag ttatctacac gacggggagt caggcaacta    6480
tggatgaacg aaatagacag atcgctgaga taggtgcctc actgattaag cattggtaac    6540
tgtcagacca agtttactca tatatacttt agattgattt aaaacttcat ttttaattta    6600
aaaggatcta ggtgaagatc ctttttgata atctcatgac caaaatccct taacgtgagt    6660
tttcgttcca ctgagcgtca gaccccgtag aaaagatcaa aggatcttct tgagatcctt    6720
tttttctgcg cgtaatctgc tgcttgcaaa caaaaaaacc accgctacca gcggtggttt    6780
gtttgccgga tcaagagcta ccaactcttt ttccgaaggt aactggcttc agcagagcgc    6840
agataccaaa tactgttctt ctagtgtagc cgtagttagg ccaccacttc aagaactctg    6900
tagcaccgcc tacatacctc gctctgctaa tcctgttacc agtggctgct gccagtggcg    6960
ataagtcgtg tcttaccggg ttggactcaa gacgatagtt accggataag gcgcagcggt    7020
cgggctgaac ggggggttcg tgcacacagc ccagcttgga gcgaacgacc tacaccgaac    7080
tgagatacct acagcgtgag ctatgagaaa gcgccacgct tcccgaaggg agaaaggcgg    7140
acaggtatcc ggtaagcggc agggtcggaa caggagagcg cacgagggag cttccagggg    7200
gaaacgcctg gtatctttat agtcctgtcg ggtttcgcca cctctgactt gagcgtcgat    7260
ttttgtgatg ctcgtcaggg gggcggagcc tatggaaaaa cgccagcaac gcggcctttt    7320
tacggttcct ggccttttgc tggccttttg ctcacatgtt ctttcctgcg ttatcccctg    7380
attctgtgga taaccgtatt accgcctttg agtgagctga taccgctcgc cgcagccgaa    7440
cgaccgagcg cagcgagtca gtgagcgagg aagcggaaga gcgcccaata cgcaaaccgc    7500
ctctccccgc gcgttggccg attcattaat gcagctggca cgacaggttt cccgactgga    7560
aagcgggcag tgagcgcaac gcaattaatg tgagttagct cactcattag gcaccccagg    7620
ctttacactt tatgcttccg gctcgtatgt tgtgtggaat tgtgagcgga taacaatttc    7680
acacaggaaa cagctatgac catgattacg ccaagcttgc atgcctgcag gcagctgcgc    7740
gctcgaactt catgcctgcc gaccttcccc aggtcacgat ccggacggcg ggtgagttca    7800
cattttarca gccggacgtg caractccgc tggtggtcta acgtcggtta ggtcccttga    7860
atcacgggac atatgttggt gttggaggt                                      7889
```

<210> SEQ ID NO 2
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 2
ggtagcgcct cagtggtgt                                                    19

<210> SEQ ID NO 3
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 3
ggcaaggagc tgtacctga                                                    19

<210> SEQ ID NO 4
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 4
gcaaggagct gtacctgaa                                                    19

<210> SEQ ID NO 5
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 5
aaggagctgt acctgagca                                                    19

<210> SEQ ID NO 6
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 6
aggagctgta cctgagcta                                                    19

<210> SEQ ID NO 7
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 7
ggaacatcat cgtgttcta                                                    19

<210> SEQ ID NO 8
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 8
ctccaaaatc aggtatgaa                                                    19

<210> SEQ ID NO 9
<211> LENGTH: 19
<212> TYPE: DNA

<213> ORGANISM: Artificial Sequence
<220> FEATURE:
<223> OTHER INFORMATION: Cypor shRNA target sequence

<400> SEQUENCE: 9
gcacccttca taggcttca                                                    19

<210> SEQ ID NO 10
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 10
gtgatttcca gtgagtgta                                                    19

<210> SEQ ID NO 11
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 11
gtggttttct gcatggcca                                                    19

<210> SEQ ID NO 12
<211> LENGTH: 23
<212> TYPE: DNA
<213> ORGANISM: Artificial Sequence
<220> FEATURE:
<223> OTHER INFORMATION: Cypor shRNA target sequence

<400> SEQUENCE: 12
gaatgggtgc ttcttgttgg act                                               23

<210> SEQ ID NO 13
<211> LENGTH: 24
<212> TYPE: DNA
<213> ORGANISM: Artificial Sequence
<220> FEATURE:
<223> OTHER INFORMATION: Cypor shRNA target sequence

<400> SEQUENCE: 13
ggccggctga agagctacga gaac                                              24

<210> SEQ ID NO 14
<211> LENGTH: 22
<212> TYPE: DNA
<213> ORGANISM: Artificial Sequence
<220> FEATURE:
<223> OTHER INFORMATION: Cypor shRNA target sequence

<400> SEQUENCE: 14
gcacctgtgg aagttgatcg aa                                                22

<210> SEQ ID NO 15
<211> LENGTH: 23
<212> TYPE: DNA
<213> ORGANISM: Artificial Sequence
<220> FEATURE:
<223> OTHER INFORMATION: Cypor shRNA target sequence

<400> SEQUENCE: 15
cctaacctac tggttcctct tct                                               23

-continued

```
<210> SEQ ID NO 16
<211> LENGTH: 24
<212> TYPE: DNA
<213> ORGANISM: Artificial Sequence
<220> FEATURE:
<223> OTHER INFORMATION: Cypor shRNA target sequence

<400> SEQUENCE: 16
cggtggccga agaagtatct cttt                                    24

<210> SEQ ID NO 17
<211> LENGTH: 21
<212> TYPE: DNA
<213> ORGANISM: Artificial Sequence
<220> FEATURE:
<223> OTHER INFORMATION: Cypor shRNA target sequence

<400> SEQUENCE: 17
gccagcgttt catgatcaac a                                       21

<210> SEQ ID NO 18
<211> LENGTH: 21
<212> TYPE: DNA
<213> ORGANISM: Artificial Sequence
<220> FEATURE:
<223> OTHER INFORMATION: Cypor shRNA target sequence

<400> SEQUENCE: 18
gaacaagacc tacgagcact t                                       21

<210> SEQ ID NO 19
<211> LENGTH: 21
<212> TYPE: DNA
<213> ORGANISM: Artificial Sequence
<220> FEATURE:
<223> OTHER INFORMATION: Cypor shRNA target sequence

<400> SEQUENCE: 19
ggaacttgga ggaggacttc a                                       21

<210> SEQ ID NO 20
<211> LENGTH: 21
<212> TYPE: DNA
<213> ORGANISM: Artificial Sequence
<220> FEATURE:
<223> OTHER INFORMATION: Cypor shRNA target sequence

<400> SEQUENCE: 20
ggatgaggag tccaacaaga a                                       21

<210> SEQ ID NO 21
<211> LENGTH: 21
<212> TYPE: DNA
<213> ORGANISM: Artificial Sequence
<220> FEATURE:
<223> OTHER INFORMATION: Cypor shRNA target sequence

<400> SEQUENCE: 21
ggcggtggac tacatcaaga a                                       21

<210> SEQ ID NO 22
<211> LENGTH: 21
<212> TYPE: DNA
<213> ORGANISM: Artificial Sequence
<220> FEATURE:
```

<223> OTHER INFORMATION: Cypor shRNA target sequence

<400> SEQUENCE: 22
gcggtggact acatcaagaa a                                                                       21

<210> SEQ ID NO 23
<211> LENGTH: 21
<212> TYPE: DNA
<213> ORGANISM: Artificial Sequence
<220> FEATURE:
<223> OTHER INFORMATION: Cypor shRNA target sequence

<400> SEQUENCE: 23
ggtggactac atcaagaaac t                                                                       21

<210> SEQ ID NO 24
<211> LENGTH: 21
<212> TYPE: DNA
<213> ORGANISM: Artificial Sequence
<220> FEATURE:
<223> OTHER INFORMATION: Cypor shRNA target sequence

<400> SEQUENCE: 24
gcccttggaa taaagttctg t                                                                       21

<210> SEQ ID NO 25
<211> LENGTH: 20
<212> TYPE: DNA
<213> ORGANISM: Artificial Sequence
<220> FEATURE:
<223> OTHER INFORMATION: Cypor shRNA target sequence

<400> SEQUENCE: 25
gccgaagaag tatctctttc                                                                         20

<210> SEQ ID NO 26
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 26
ggttcctctt cagaaagaa                                                                          19

<210> SEQ ID NO 27
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 27
ggtggactac atcaagaaa                                                                          19

<210> SEQ ID NO 28
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 28
gctgccagcg tttcatgat                                                                          19

-continued

```
<210> SEQ ID NO 29
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 29
gccagcgttt catgatcaa                                                        19

<210> SEQ ID NO 30
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 30
ggccgaagaa gtatctctt                                                        19

<210> SEQ ID NO 31
<211> LENGTH: 20
<212> TYPE: DNA
<213> ORGANISM: Artificial Sequence
<220> FEATURE:
<223> OTHER INFORMATION: Cypor shRNA target sequence

<400> SEQUENCE: 31
ggccgtgtgt gaacactttg                                                       20

<210> SEQ ID NO 32
<211> LENGTH: 19
<212> TYPE: DNA
<213> ORGANISM: Artificial Sequence
<220> FEATURE:
<223> OTHER INFORMATION: Cypor shRNA target sequence

<400> SEQUENCE: 32
ggaggaacat catcgtgtt                                                        19

<210> SEQ ID NO 33
<211> LENGTH: 20
<212> TYPE: DNA
<213> ORGANISM: Artificial Sequence
<220> FEATURE:
<223> OTHER INFORMATION: Cypor shRNA target sequence

<400> SEQUENCE: 33
ggtcaagttc gcggtgtttg                                                       20

<210> SEQ ID NO 34
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 34
tacagcacgt tggtacgcgg cgg                                                   23

<210> SEQ ID NO 35
<211> LENGTH: 23
<212> TYPE: DNA
<213> ORGANISM: Artificial Sequence
<220> FEATURE:
<223> OTHER INFORMATION: Cypor CRISPR target sequences
```

```
<400> SEQUENCE: 35
tggccgcatc aacaagggcg tgg                                              23

<210> SEQ ID NO 36
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 36
tcataggctt catccaggag cgg                                              23

<210> SEQ ID NO 37
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 37
ctgtggaagt tgatcgaagg cgg                                              23

<210> SEQ ID NO 38
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 38
tgcggccaag gtgtacatgg ggg                                              23

<210> SEQ ID NO 39
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 39
acaggtagtc ctcatccgag cgg                                              23

<210> SEQ ID NO 40
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 40
tgggcaagta cgtggacaag cgg                                              23

<210> SEQ ID NO 41
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 41
tagtagcggg cctgcaggcg cgg                                              23

<210> SEQ ID NO 42
<211> LENGTH: 23
```

-continued

```
<212> TYPE: DNA
<213> ORGANISM: Artificial Sequence
<220> FEATURE:
<223> OTHER INFORMATION: Cypor CRISPR target sequences

<400> SEQUENCE: 42
gtcccacaag gtgagacggg cgg                                                    23

<210> SEQ ID NO 43
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 43
acggattctt ggcatcaaag ggg                                                    23

<210> SEQ ID NO 44
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 44
ggtccacacc gacatagatg cgg                                                    23

<210> SEQ ID NO 45
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 45
tgaggcgatg gagtagtagc ggg                                                    23

<210> SEQ ID NO 46
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 46
tgttctacgg ctcccagacg ggg                                                    23

<210> SEQ ID NO 47
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 47
gatgcggcca aggtgtacat ggg                                                    23

<210> SEQ ID NO 48
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 48
```

-continued cctgtcatca tggtgggccc cgg                                                        23

<210> SEQ ID NO 49
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 49
tgcctcgcat cccgtagcgg tgg                                                        23

<210> SEQ ID NO 50
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 50
gcctcgcatc ccgtagcggt ggg                                                        23

<210> SEQ ID NO 51
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 51
cgaacatggg caccagcgca cgg                                                        23

<210> SEQ ID NO 52
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 52
ccctggacgt gtggagctag ggg                                                        23

<210> SEQ ID NO 53
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 53
ggttctcgta gctcttcagc cgg                                                        23

<210> SEQ ID NO 54
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 54
agggccgtgc ggtaggacgt agg                                                        23

<210> SEQ ID NO 55
<211> LENGTH: 23
<212> TYPE: DNA
<213> ORGANISM: Artificial Sequence -continued

```
<220> FEATURE:
<223> OTHER INFORMATION: Cypor CRISPR target sequences

<400> SEQUENCE: 55
cgtgttctac ggctcccaga cgg                                              23

<210> SEQ ID NO 56
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 56
tcgtacagca cgttggtacg cgg                                              23

<210> SEQ ID NO 57
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 57
gtgcggtagg acgtagggca cgg                                              23

<210> SEQ ID NO 58
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 58
ctacgagcac ttcaatgcca tgg                                              23

<210> SEQ ID NO 59
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 59
tgcggtagga cgtagggcac ggg                                              23

<210> SEQ ID NO 60
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 60
acatgcctcg catcccgtag cgg                                              23

<210> SEQ ID NO 61
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 61
agcagtccca caaggtgaga cgg                                              23
```

-continued

```
<210> SEQ ID NO 62
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 62
atgaggcgat ggagtagtag cgg                                              23

<210> SEQ ID NO 63
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 63
caagtacgtg gacaagcggc tgg                                              23

<210> SEQ ID NO 64
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 64
atgcggccaa ggtgtacatg ggg                                              23

<210> SEQ ID NO 65
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 65
atcatggtgg gccccggcac cgg                                              23

<210> SEQ ID NO 66
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 66
gccagagatc gacaacgccc tgg                                              23

<210> SEQ ID NO 67
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 67
tgggacttgc gcacgaacat ggg                                              23

<210> SEQ ID NO 68
<211> LENGTH: 23
<212> TYPE: DNA
<213> ORGANISM: Artificial Sequence
<220> FEATURE:
<223> OTHER INFORMATION: Cypor CRISPR target sequences
```

-continued

<400> SEQUENCE: 68
tccacacgtc cagggagtag cgg                                              23

<210> SEQ ID NO 69
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 69
caccgacata gatgcggcca agg                                              23

<210> SEQ ID NO 70
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 70
ggggagacgc tgctgtacta cgg                                              23

<210> SEQ ID NO 71
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 71
agagatcgac aacgccctgg tgg                                              23

<210> SEQ ID NO 72
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 72
ggtacagctc ctaagagaca cgg                                              23

<210> SEQ ID NO 73
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 73
acagcacgtt ggtacgcggc ggg                                              23

<210> SEQ ID NO 74
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 74
cgtactggcg aatgctggaa agg                                              23

<210> SEQ ID NO 75

-continued

<210> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 75
gtgccctacg tcctaccgca cgg                                                              23

<210> SEQ ID NO 76
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 76
tccaaggacg cccaccgcta cgg                                                              23

<210> SEQ ID NO 77
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 77
tcccacaagg tgagacgggc ggg                                                              23

<210> SEQ ID NO 78
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 78
taggacgtag ggcacgggaa tgg                                                              23

<210> SEQ ID NO 79
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 79
caccccaaag tgttcacaca cgg                                                              23

<210> SEQ ID NO 80
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 80
gcagtcccac aaggtgagac ggg                                                              23

<210> SEQ ID NO 81
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 81

-continued ggacttctac gactggctgc agg                                    23

<210> SEQ ID NO 82
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 82
tcgtgggtct cctaacctac tgg                                    23

<210> SEQ ID NO 83
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 83
ctctgctctc gtcaaccagc tgg                                    23

<210> SEQ ID NO 84
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 84
tctctctggg gtcaagttcg cgg                                    23

<210> SEQ ID NO 85
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 85
cggatgagga ctacctgtac cgg                                    23

<210> SEQ ID NO 86
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 86
cgccttcgat caacttccac agg                                    23

<210> SEQ ID NO 87
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 87
gtaggtgagg gccgtgcggt agg                                    23

<210> SEQ ID NO 88
<211> LENGTH: 23
<212> TYPE: DNA

-continued

```
<213> ORGANISM: Artificial Sequence
<220> FEATURE:
<223> OTHER INFORMATION: Cypor CRISPR target sequences

<400> SEQUENCE: 88
ctgggacttg cgcacgaaca tgg                                                    23

<210> SEQ ID NO 89
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 89
atgtccctga acaacctgga tgg                                                    23

<210> SEQ ID NO 90
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 90
ccaaggacgc ccaccgctac ggg                                                    23

<210> SEQ ID NO 91
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 91
caccttggcc gcatctatgt cgg                                                    23

<210> SEQ ID NO 92
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 92
gcctatgaag ggtgccaccc cgg                                                    23

<210> SEQ ID NO 93
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 93
tccctccagg tatgaatctg ggg                                                    23

<210> SEQ ID NO 94
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 94
tggccgcatc tatgtcggtg tgg                                                    23
```

-continued

```
<210> SEQ ID NO 95
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 95
gcagtacgcc tcggagccct cgg                                          23

<210> SEQ ID NO 96
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 96
cattcgccag tacgagcttg tgg                                          23

<210> SEQ ID NO 97
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 97
aggaacatca tcgtgttcta cgg                                          23

<210> SEQ ID NO 98
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 98
cacgttggta cgcggcgggt tgg                                          23

<210> SEQ ID NO 99
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 99
ctcagccacg atgtcgtaga agg                                          23

<210> SEQ ID NO 100
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 100
gtctgaattt tggtgaactc ggg                                          23

<210> SEQ ID NO 101
<211> LENGTH: 23
<212> TYPE: DNA
<213> ORGANISM: Artificial Sequence
<220> FEATURE:
```

<223> OTHER INFORMATION: Cypor CRISPR target sequences

<400> SEQUENCE: 101
gtccagggag tagcggccct tgg                                              23

<210> SEQ ID NO 102
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 102
gtgttctacg gctcccagac ggg                                              23

<210> SEQ ID NO 103
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 103
cggttccctg gttcagcttc cgg                                              23

<210> SEQ ID NO 104
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 104
gcacctggaa ttggacatct cgg                                              23

<210> SEQ ID NO 105
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 105
tacgacatcg tggctgagct cgg                                              23

<210> SEQ ID NO 106
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 106
tcttcctgcc cagggatgca cgg                                              23

<210> SEQ ID NO 107
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 107
caactctgtg cacatctgtg cgg                                              23

-continued

```
<210> SEQ ID NO 108
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 108
gcccgcccgt ctcaccttgt ggg                                          23

<210> SEQ ID NO 109
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 109
gtagaagtcc tgggcattgt cgg                                          23

<210> SEQ ID NO 110
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 110
gtactacggc tgccgccgct cgg                                          23

<210> SEQ ID NO 111
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 111
gcacgcggtg gcagcttacc agg                                          23

<210> SEQ ID NO 112
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 112
ggtagtcctc atccgagcgg cgg                                          23

<210> SEQ ID NO 113
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 113
cataggcttc atccaggagc ggg                                          23

<210> SEQ ID NO 114
<211> LENGTH: 23
<212> TYPE: DNA
<213> ORGANISM: Artificial Sequence
<220> FEATURE:
<223> OTHER INFORMATION: Cypor CRISPR target sequences
```

-continued

```
<400> SEQUENCE: 114
aaggctggcc gcatcaacaa ggg                                             23

<210> SEQ ID NO 115
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 115
atggcctcct cctccggcga ggg                                             23

<210> SEQ ID NO 116
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 116
aaacacctgc gtggacacag ggg                                             23

<210> SEQ ID NO 117
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 117
cgagctggcg cagtacgcct cgg                                             23

<210> SEQ ID NO 118
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 118
gcgtggccac caactggctg cgg                                             23

<210> SEQ ID NO 119
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 119
cgggatgcga ggcatgtcag cgg                                             23

<210> SEQ ID NO 120
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 120
ctggggttgg gcgacgacga tgg                                             23

<210> SEQ ID NO 121
<211> LENGTH: 23
```

<212> TYPE: DNA
<213> ORGANISM: Artificial Sequence
<220> FEATURE:
<223> OTHER INFORMATION: Cypor CRISPR target sequences

<400> SEQUENCE: 121
tactggcgaa tgctggaaag ggg                                          23

<210> SEQ ID NO 122
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 122
tcacctggac tcctcgccag tgg                                          23

<210> SEQ ID NO 123
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 123
tggtggcctt gaagggcagg cgg                                          23

<210> SEQ ID NO 124
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 124
taccaacgtg ctgtacgagc tgg                                          23

<210> SEQ ID NO 125
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 125
cacctgtgga agttgatcga agg                                          23

<210> SEQ ID NO 126
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 126
caacatggga gactcccacg tgg                                          23

<210> SEQ ID NO 127
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 127

-continued gtactggcga atgctggaaa ggg                                                    23

<210> SEQ ID NO 128
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 128
ggacatgacg acgtccaggt cgg                                                    23

<210> SEQ ID NO 129
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 129
tggaggagga cttcatcacc tgg                                                    23

<210> SEQ ID NO 130
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 130
ggtaagctgc caccgcgtgc tgg                                                    23

<210> SEQ ID NO 131
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 131
tgtacatggg ggagatgggc cgg                                                    23

<210> SEQ ID NO 132
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 132
tgcatggcca cctacggtga ggg                                                    23

<210> SEQ ID NO 133
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 133
gtatgaatct ggggaccacg tgg                                                    23

<210> SEQ ID NO 134
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 134
tggctgcagt caccaccaac cgg                                                        23

<210> SEQ ID NO 135
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 135
cgacatcgtg gctgagctcg ggg                                                        23

<210> SEQ ID NO 136
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 136
agtgccggcc ctcaccttgg agg                                                        23

<210> SEQ ID NO 137
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 137
cttgttgatg cggccagcct tgg                                                        23

<210> SEQ ID NO 138
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 138
ctggcgagag cagttctggc cgg                                                        23

<210> SEQ ID NO 139
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 139
tcaggtcggc ctgcagaaac agg                                                        23

<210> SEQ ID NO 140
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 140
agccacgctc cctccactca cgg                                                        23

-continued

```
<210> SEQ ID NO 141
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 141
attctgtttt cgctcatcgt ggg                                        23

<210> SEQ ID NO 142
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 142
caccaactgg ctgcgggcca agg                                        23

<210> SEQ ID NO 143
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 143
gaacaccttc tacgacatcg tgg                                        23

<210> SEQ ID NO 144
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 144
tacgagcact tcaatgccat ggg                                        23

<210> SEQ ID NO 145
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 145
gtacagctcc taagagacac ggg                                        23

<210> SEQ ID NO 146
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 146
tggccacgcc cttgttgatg cgg                                        23

<210> SEQ ID NO 147
<211> LENGTH: 23
<212> TYPE: DNA
<213> ORGANISM: Artificial Sequence
<220> FEATURE:
<223> OTHER INFORMATION: Cypor CRISPR target sequences
```

-continued

```
<400> SEQUENCE: 147
atgcccagga cttctacgac tgg                                          23

<210> SEQ ID NO 148
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 148
caggtgcatg aggtggcgct cgg                                          23

<210> SEQ ID NO 149
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 149
cgagaaccag aagccgtgag tgg                                          23

<210> SEQ ID NO 150
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 150
agtcctgggc attgtcggtg ggg                                          23

<210> SEQ ID NO 151
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 151
gggcgttgtc gatctctggc agg                                          23

<210> SEQ ID NO 152
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 152
ctcacccaca gacgtagatg tgg                                          23

<210> SEQ ID NO 153
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 153
ttcggccacc gcctcggaca cgg                                          23

<210> SEQ ID NO 154
```

-continued

```
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 154
tacttcttcg gccaccgcct cgg                                                    23

<210> SEQ ID NO 155
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 155
acgatgatgt tcctcccta agg                                                     23

<210> SEQ ID NO 156
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 156
aggagctggc gcagttccac agg                                                    23

<210> SEQ ID NO 157
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 157
caaacacctg cgtggacaca ggg                                                    23

<210> SEQ ID NO 158
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 158
tggggttggg cgacgacgat ggg                                                    23

<210> SEQ ID NO 159
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 159
tctgctctcg tcaaccagct ggg                                                    23

<210> SEQ ID NO 160
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 160
```

-continued

```
ctggttcagc ttccggttgg tgg                                              23

<210> SEQ ID NO 161
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 161
gattctgttt tcgctcatcg tgg                                              23

<210> SEQ ID NO 162
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 162
ccggccgtgt gtgaacactt tgg                                              23

<210> SEQ ID NO 163
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 163
ggccgtgtgt gaacactttg ggg                                              23

<210> SEQ ID NO 164
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 164
ctccctggac gtgtggagct agg                                              23

<210> SEQ ID NO 165
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 165
gggccgtgcg gtaggacgta ggg                                              23

<210> SEQ ID NO 166
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 166
gactgtggca ctcaccatcc agg                                              23

<210> SEQ ID NO 167
<211> LENGTH: 23
<212> TYPE: DNA
```

<213> ORGANISM: Artificial Sequence
<220> FEATURE:
<223> OTHER INFORMATION: Cypor CRISPR target sequences

<400> SEQUENCE: 167
ttaggagctg tacctgagct ggg                                                             23

<210> SEQ ID NO 168
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 168
cggccagaac tgctctcgcc agg                                                             23

<210> SEQ ID NO 169
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 169
gcccctagct ccacacgtcc agg                                                             23

<210> SEQ ID NO 170
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 170
gaccaagggc cgctactccc tgg                                                             23

<210> SEQ ID NO 171
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 171
ctccttggcc cgcagccagt tgg                                                             23

<210> SEQ ID NO 172
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 172
tgcccgcccg tctcaccttg tgg                                                             23

<210> SEQ ID NO 173
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 173
tgaggtggcg ctcggttccc tgg                                                             23

```
<210> SEQ ID NO 174
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 174
accagggcgt tgtcgatctc tgg                                          23

<210> SEQ ID NO 175
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 175
ggatgaggac tacctgtacc ggg                                          23

<210> SEQ ID NO 176
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 176
tcaccttgtg ggactgctcc cgg                                          23

<210> SEQ ID NO 177
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 177
atctcacccc cgtgtctctt agg                                          23

<210> SEQ ID NO 178
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 178
catggagcac gcgcaggcgg tgg                                          23

<210> SEQ ID NO 179
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 179
gcgcaccttg ccctcgccgg agg                                          23

<210> SEQ ID NO 180
<211> LENGTH: 23
<212> TYPE: DNA
<213> ORGANISM: Artificial Sequence
<220> FEATURE:
```

<223> OTHER INFORMATION: Cypor CRISPR target sequences

<400> SEQUENCE: 180
gatggcctcc tcctccggcg agg                          23

<210> SEQ ID NO 181
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 181
tcgatggggg gccgcaggga cgg                          23

<210> SEQ ID NO 182
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 182
ggagaacggc ggccgtgcgc tgg                          23

<210> SEQ ID NO 183
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 183
gaagggtgcc accccggtgc cgg                          23

<210> SEQ ID NO 184
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 184
gcccaccgct acgggatgcg agg                          23

<210> SEQ ID NO 185
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 185
gggtgagcgc accgtccctg tgg                          23

<210> SEQ ID NO 186
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 186
cgacgtccag gtcggcaccc agg                          23

-continued

```
<210> SEQ ID NO 187
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 187
tgcgctcacc cagctcaacg tgg                                              23

<210> SEQ ID NO 188
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 188
caaggctggc cgcatcaaca agg                                              23

<210> SEQ ID NO 189
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 189
gttttctgca tggccaccta cgg                                              23

<210> SEQ ID NO 190
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 190
cttaccaggt catactcctc agg                                              23

<210> SEQ ID NO 191
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 191
ctctgtgcac atctgtgcgg tgg                                              23

<210> SEQ ID NO 192
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 192
gcgtggtggc cttgaagggc agg                                              23

<210> SEQ ID NO 193
<211> LENGTH: 23
<212> TYPE: DNA
<213> ORGANISM: Artificial Sequence
<220> FEATURE:
<223> OTHER INFORMATION: Cypor CRISPR target sequences
```

-continued

```
<400> SEQUENCE: 193
tcatcctcca aggtgagggc cgg                                                    23

<210> SEQ ID NO 194
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 194
ctgcatggcc acctacggtg agg                                                    23

<210> SEQ ID NO 195
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 195
accaaccgga agctgaacca ggg                                                    23

<210> SEQ ID NO 196
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 196
accccagctc aaagatgcgc tgg                                                    23

<210> SEQ ID NO 197
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 197
tctgaatttt ggtgaactcg ggg                                                    23

<210> SEQ ID NO 198
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 198
ctcccgggag cagtcccaca agg                                                    23

<210> SEQ ID NO 199
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 199
cttaggagct gtacctgagc tgg                                                    23

<210> SEQ ID NO 200
<211> LENGTH: 23
```

```
<212> TYPE: DNA
<213> ORGANISM: Artificial Sequence
<220> FEATURE:
<223> OTHER INFORMATION: Cypor CRISPR target sequences

<400> SEQUENCE: 200
gttgacgaga gcagagtcgt tgg                                              23

<210> SEQ ID NO 201
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 201
tcagggacat gacgacgtcc agg                                              23

<210> SEQ ID NO 202
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 202
aaggagcctg ccggggagaa cgg                                              23

<210> SEQ ID NO 203
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 203
caatgccatg ggcaagtacg tgg                                              23

<210> SEQ ID NO 204
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 204
accggggtgg cacccttcat agg                                              23

<210> SEQ ID NO 205
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 205
cgccagctcg tacagcacgt tgg                                              23

<210> SEQ ID NO 206
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 206
```
acgacatcgt ggctgagctc ggg                                                    23

<210> SEQ ID NO 207
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 207
cgagagcaga gtcgttggct ggg                                                    23

<210> SEQ ID NO 208
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 208
ggtagtaggt gagggccgtg cgg                                                    23

<210> SEQ ID NO 209
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 209
agcaagaccg agagcacctg tgg                                                    23

<210> SEQ ID NO 210
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 210
cgcaagatgg cctcctcctc cgg                                                    23

<210> SEQ ID NO 211
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 211
cggtggagct ggtgtccacg tgg                                                    23

<210> SEQ ID NO 212
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 212
cagccagtcg tagaagtcct ggg                                                    23

<210> SEQ ID NO 213
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 213
tcctggatga agcctatgaa ggg                                                            23

<210> SEQ ID NO 214
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 214
acgagagcag agtcgttggc tgg                                                            23

<210> SEQ ID NO 215
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 215
gacaagcggc tggagcagct cgg                                                            23

<210> SEQ ID NO 216
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 216
ggatggccag gatgtgcctc cgg                                                            23

<210> SEQ ID NO 217
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 217
ccagttccgc ctgcccttca agg                                                            23

<210> SEQ ID NO 218
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 218
gcagccagtc gtagaagtcc tgg                                                            23

<210> SEQ ID NO 219
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 219
agctcacaca ggtggtcgat ggg                                                            23

-continued

```
<210> SEQ ID NO 220
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 220
gctctcggtc ttgctttagc agg                                               23

<210> SEQ ID NO 221
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 221
tccacgcagg tgtttggtct tgg                                               23

<210> SEQ ID NO 222
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 222
ccacgcaggt gtttggtctt ggg                                               23

<210> SEQ ID NO 223
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 223
actcaccatc caggttgttc agg                                               23

<210> SEQ ID NO 224
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 224
tcaacttcca caggtgctct cgg                                               23

<210> SEQ ID NO 225
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 225
cacctccttg cctgcgtggc agg                                               23

<210> SEQ ID NO 226
<211> LENGTH: 23
<212> TYPE: DNA
<213> ORGANISM: Artificial Sequence
<220> FEATURE:
<223> OTHER INFORMATION: Cypor CRISPR target sequences
```

<400> SEQUENCE: 226
tgcagccagg aacggattct tgg                                                    23

<210> SEQ ID NO 227
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 227
cggctgccgc cgctcggatg agg                                                    23

<210> SEQ ID NO 228
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 228
ggccaccgcc tcggacacgg tgg                                                    23

<210> SEQ ID NO 229
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 229
cttgcctgcg tggcaggggc cgg                                                    23

<210> SEQ ID NO 230
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 230
cgcacggccg ccgttctccc cgg                                                    23

<210> SEQ ID NO 231
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 231
caccgcctgc gcgtgctcca tgg                                                    23

<210> SEQ ID NO 232
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 232
gctgaaaaga gatacttctt cgg                                                    23

<210> SEQ ID NO 233

-continued

```
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 233
tgcgggccaa ggagcctgcc ggg                                              23

<210> SEQ ID NO 234
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 234
cagctccacc gtgtccgagg cgg                                              23

<210> SEQ ID NO 235
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 235
ggtggggtct ccctcaccgt agg                                              23

<210> SEQ ID NO 236
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 236
gtggagtacg agaccaaggc tgg                                              23

<210> SEQ ID NO 237
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 237
agcggtgggc gtccttggac agg                                              23

<210> SEQ ID NO 238
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 238
caccttgtgg gactgctccc ggg                                              23

<210> SEQ ID NO 239
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 239
```
caaaatcctg ggtgccgacc tgg                                            23

<210> SEQ ID NO 240
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 240
ggccatggag cacgcgcagg cgg                                            23

<210> SEQ ID NO 241
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 241
acagctccta agagacacgg ggg                                            23

<210> SEQ ID NO 242
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 242
ctgccacgca ggcaaggagg tgg                                            23

<210> SEQ ID NO 243
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 243
tgaggactac ctgtaccggg agg                                            23

<210> SEQ ID NO 244
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 244
aggtgctgga cgtagacctg ggg                                            23

<210> SEQ ID NO 245
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 245
cccagcgcat ctttgagctg ggg                                            23

<210> SEQ ID NO 246
<211> LENGTH: 23
<212> TYPE: DNA

<213> ORGANISM: Artificial Sequence
<220> FEATURE:
<223> OTHER INFORMATION: Cypor CRISPR target sequences

<400> SEQUENCE: 246
tacagctcct aagagacacg ggg                                                    23

<210> SEQ ID NO 247
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 247
ggtggagctg gtgtccacgt ggg                                                    23

<210> SEQ ID NO 248
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 248
ggccatgcag aaaaccacca ggg                                                    23

<210> SEQ ID NO 249
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 249
gtggtgactg cagccaggaa cgg                                                    23

<210> SEQ ID NO 250
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 250
agaccccacc gacaatgccc agg                                                    23

<210> SEQ ID NO 251
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 251
gtgggactgc tcccgggaga agg                                                    23

<210> SEQ ID NO 252
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 252
tcacccacag acgtagatgt ggg                                                    23

```
<210> SEQ ID NO 253
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 253
ggagctggcg cagttccaca ggg                                              23

<210> SEQ ID NO 254
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 254
gccatgttcc gtgcatccct ggg                                              23

<210> SEQ ID NO 255
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 255
ctttctgaag aggaaccagt agg                                              23

<210> SEQ ID NO 256
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 256
cgcctcatcc tccaaggtga ggg                                              23

<210> SEQ ID NO 257
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 257
cttgtccacg tacttgccca tgg                                              23

<210> SEQ ID NO 258
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 258
ctctggcagg ctgctcaggt cgg                                              23

<210> SEQ ID NO 259
<211> LENGTH: 23
<212> TYPE: DNA
<213> ORGANISM: Artificial Sequence
<220> FEATURE:
```

-continued

<223> OTHER INFORMATION: Cypor CRISPR target sequences

<400> SEQUENCE: 259
gctgcgacag cagggtgagt ggg                                                    23

<210> SEQ ID NO 260
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 260
ctcctggatg aagcctatga agg                                                    23

<210> SEQ ID NO 261
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 261
catggcattg aagtgctcgt agg                                                    23

<210> SEQ ID NO 262
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 262
tgcaggactg cccgtccctg cgg                                                    23

<210> SEQ ID NO 263
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 263
ttggcatcaa aggggctggg tgg                                                    23

<210> SEQ ID NO 264
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 264
gcccagggat gcacggaaca tgg                                                    23

<210> SEQ ID NO 265
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 265
tggagtagta gcgggcctgc agg                                                    23

<210> SEQ ID NO 266
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 266
gatgaagtcc tcctccaagc tgg                                                                       23

<210> SEQ ID NO 267
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 267
tgccacgcag gcaaggaggt ggg                                                                       23

<210> SEQ ID NO 268
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 268
cgtcatgtcc ctgaacaacc tgg                                                                       23

<210> SEQ ID NO 269
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 269
cgcccagcgc atctttgagc tgg                                                                       23

<210> SEQ ID NO 270
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 270
ggcgtccttg gacaggcggt tgg                                                                       23

<210> SEQ ID NO 271
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 271
gcggcgggtt ggtgatgtcc agg                                                                       23

<210> SEQ ID NO 272
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 272
gacagacgtg gatctctctg ggg                                                                     23

<210> SEQ ID NO 273
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 273
ctgcgacagc agggtgagtg ggg                                                                     23

<210> SEQ ID NO 274
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 274
ggtcttgctt tagcaggtgc tgg                                                                     23

<210> SEQ ID NO 275
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 275
tccctggttc agcttccggt tgg                                                                     23

<210> SEQ ID NO 276
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 276
accacgcctg tcatcatggt ggg                                                                     23

<210> SEQ ID NO 277
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 277
cagagttggg gtggacctgt ggg                                                                     23

<210> SEQ ID NO 278
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 278
gctcaacgtg gccttctccc ggg                                                                     23

<210> SEQ ID NO 279
<211> LENGTH: 23

-continued

```
<212> TYPE: DNA
<213> ORGANISM: Artificial Sequence
<220> FEATURE:
<223> OTHER INFORMATION: Cypor CRISPR target sequences

<400> SEQUENCE: 279
cgcacagatg tgcacagagt tgg                                              23

<210> SEQ ID NO 280
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 280
cgagcgccac ctcatgcacc tgg                                              23

<210> SEQ ID NO 281
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 281
tccccagatt catacctgga ggg                                              23

<210> SEQ ID NO 282
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 282
tgaagaggaa ccagtaggtt agg                                              23

<210> SEQ ID NO 283
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 283
ctccctccag gtatgaatct ggg                                              23

<210> SEQ ID NO 284
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 284
gttggtgatg tccaggtagt agg                                              23

<210> SEQ ID NO 285
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 285
```

-continued

```
tccctggacg tgtggagcta ggg                                          23

<210> SEQ ID NO 286
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 286
agctcaacgt ggccttctcc cgg                                          23

<210> SEQ ID NO 287
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 287
agatgcggcc aaggtgtaca tgg                                          23

<210> SEQ ID NO 288
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 288
ctcaccatcc aggttgttca ggg                                          23

<210> SEQ ID NO 289
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 289
cggccgtgtg tgaacacttt ggg                                          23

<210> SEQ ID NO 290
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 290
cggggccatg gagcacgcgc agg                                          23

<210> SEQ ID NO 291
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 291
ctccaccgtg tccgaggcgg tgg                                          23

<210> SEQ ID NO 292
<211> LENGTH: 23
<212> TYPE: DNA
<213> ORGANISM: Artificial Sequence
```

<220> FEATURE:
<223> OTHER INFORMATION: Cypor CRISPR target sequences

<400> SEQUENCE: 292
catggtgggc cccggcaccg ggg                                                              23

<210> SEQ ID NO 293
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 293
ctgcgggcca aggagcctgc cgg                                                              23

<210> SEQ ID NO 294
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 294
gcgccagctc ctcccggtac agg                                                              23

<210> SEQ ID NO 295
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 295
agtatctctt ttcagcatga cgg                                                              23

<210> SEQ ID NO 296
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 296
tgtctgaatt ttggtgaact cgg                                                              23

<210> SEQ ID NO 297
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 297
cgtgtgtgaa cactttgggg tgg                                                              23

<210> SEQ ID NO 298
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 298
gtgtctgcct tccttagggg agg                                                              23

-continued

```
<210> SEQ ID NO 299
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 299
tgtggaccac aagctcgtac tgg                                             23

<210> SEQ ID NO 300
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 300
aaccagctgg gcaaaatcct ggg                                             23

<210> SEQ ID NO 301
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 301
gtgcccacat ctacgtctgt ggg                                             23

<210> SEQ ID NO 302
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 302
caccaaccgg aagctgaacc agg                                             23

<210> SEQ ID NO 303
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 303
attgcacact tttgtcttgc agg                                             23

<210> SEQ ID NO 304
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 304
tgatgttcct cccctaagga agg                                             23

<210> SEQ ID NO 305
<211> LENGTH: 23
<212> TYPE: DNA
<213> ORGANISM: Artificial Sequence
<220> FEATURE:
<223> OTHER INFORMATION: Cypor CRISPR target sequences
```

```
<400> SEQUENCE: 305
caggtgctgg acgtagacct ggg                                    23

<210> SEQ ID NO 306
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 306
ctggagggag atgtgaggct cgg                                    23

<210> SEQ ID NO 307
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 307
ctcccagacg gggactgcag agg                                    23

<210> SEQ ID NO 308
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 308
catctccccc atgtacacct tgg                                    23

<210> SEQ ID NO 309
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 309
cggcctgcag aaacagggac agg                                    23

<210> SEQ ID NO 310
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 310
ctcacacagg tggtcgatgg ggg                                    23

<210> SEQ ID NO 311
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 311
caccagctcc accgtgtccg agg                                    23

<210> SEQ ID NO 312
```

-continued

```
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 312
gatggccagg atgtgcctcc ggg                                              23

<210> SEQ ID NO 313
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 313
tgtccaattc caggtgcatg agg                                              23

<210> SEQ ID NO 314
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 314
acatctcgga ctccaaaatc agg                                              23

<210> SEQ ID NO 315
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 315
gtttgccaac cgcctgtcca agg                                              23

<210> SEQ ID NO 316
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 316
agtccgagat gtccaattcc agg                                              23

<210> SEQ ID NO 317
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 317
ggctgcgaca gcagggtgag tgg                                              23

<210> SEQ ID NO 318
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 318
```

-continued aggacgtagg gcacgggaat ggg                                                                     23

<210> SEQ ID NO 319
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 319
cgcatctttg agctggggtt ggg                                                                     23

<210> SEQ ID NO 320
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 320
ccacctcatg cacctggaat tgg                                                                     23

<210> SEQ ID NO 321
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 321
ctccatcgcc tcatcctcca agg                                                                     23

<210> SEQ ID NO 322
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 322
agagttgggg tggacctgtg ggg                                                                     23

<210> SEQ ID NO 323
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 323
gcacatctgt gcggtggttg tgg                                                                     23

<210> SEQ ID NO 324
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 324
gccgctactc cctggacgtg tgg                                                                     23

<210> SEQ ID NO 325
<211> LENGTH: 23
<212> TYPE: DNA

```
<213> ORGANISM: Artificial Sequence
<220> FEATURE:
<223> OTHER INFORMATION: Cypor CRISPR target sequences

<400> SEQUENCE: 325
ggccatgttc cgtgcatccc tgg                                        23

<210> SEQ ID NO 326
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 326
gttctccccg gcaggctcct tgg                                        23

<210> SEQ ID NO 327
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 327
actcctctgc agtccccgtc tgg                                        23

<210> SEQ ID NO 328
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 328
gagacagacg tggatctctc tgg                                        23

<210> SEQ ID NO 329
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 329
gagcctgccg gggagaacgg cgg                                        23

<210> SEQ ID NO 330
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 330
agggtgccac cccggtgccg ggg                                        23

<210> SEQ ID NO 331
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 331
agcggcccct gtgtccacgc agg                                        23
```

<210> SEQ ID NO 332
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 332
gcgggcctgg ctgcgacagc agg                                    23

<210> SEQ ID NO 333
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 333
cgcctcggag ccctcggagc agg                                    23

<210> SEQ ID NO 334
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 334
gtggtcgatg gggggccgca ggg                                    23

<210> SEQ ID NO 335
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 335
tcatggtggg ccccggcacc ggg                                    23

<210> SEQ ID NO 336
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 336
ggcagtgccg gccctcacct tgg                                    23

<210> SEQ ID NO 337
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 337
cgtggccacc aactggctgc ggg                                    23

<210> SEQ ID NO 338
<211> LENGTH: 23
<212> TYPE: DNA
<213> ORGANISM: Artificial Sequence
<220> FEATURE:

-continued

<223> OTHER INFORMATION: Cypor CRISPR target sequences

<400> SEQUENCE: 338
caggtcggcc tgcagaaaca ggg                                                    23

<210> SEQ ID NO 339
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 339
cactttgggg tggaagccac tgg                                                    23

<210> SEQ ID NO 340
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 340
ttaccaggtc atactcctca ggg                                                    23

<210> SEQ ID NO 341
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 341
ggtgcccaca tctacgtctg tgg                                                    23

<210> SEQ ID NO 342
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 342
agacagacgt ggatctctct ggg                                                    23

<210> SEQ ID NO 343
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 343
ctcctctgca gtccccgtct ggg                                                    23

<210> SEQ ID NO 344
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 344
gaacggattc ttggcatcaa agg                                                    23

```
<210> SEQ ID NO 345
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 345
atcaagaaac tgatgaccaa ggg                                                23

<210> SEQ ID NO 346
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 346
ggtggtcgat gggggccgc agg                                                 23

<210> SEQ ID NO 347
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 347
aacagtttca tgatcaacat ggg                                                23

<210> SEQ ID NO 348
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 348
ccaggtgagc aagtgcccgc agg                                                23

<210> SEQ ID NO 349
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 349
tggggtggaa gccactggcg agg                                                23

<210> SEQ ID NO 350
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 350
ggtgggcgtc cttggacagg cgg                                                23

<210> SEQ ID NO 351
<211> LENGTH: 23
<212> TYPE: DNA
<213> ORGANISM: Artificial Sequence
<220> FEATURE:
<223> OTHER INFORMATION: Cypor CRISPR target sequences
```

<400> SEQUENCE: 351
ggttgtggag tacgagacca agg                                                    23

<210> SEQ ID NO 352
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 352
tgttccgtgc atccctgggc agg                                                    23

<210> SEQ ID NO 353
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 353
ggtcctgtcc ctgtttctgc agg                                                    23

<210> SEQ ID NO 354
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 354
caaggtgtac atgggggaga tgg                                                    23

<210> SEQ ID NO 355
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 355
gcgcatcttt gagctggggt tgg                                                    23

<210> SEQ ID NO 356
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 356
cctgtgtctg ccttccttag ggg                                                    23

<210> SEQ ID NO 357
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 357
ggacgtagac ctggggccaa ggg                                                    23

<210> SEQ ID NO 358
<211> LENGTH: 23

```
<212> TYPE: DNA
<213> ORGANISM: Artificial Sequence
<220> FEATURE:
<223> OTHER INFORMATION: Cypor CRISPR target sequences

<400> SEQUENCE: 358
acctccttgc ctgcgtggca ggg                                                    23

<210> SEQ ID NO 359
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 359
cttgaagggc aggcggaact ggg                                                    23

<210> SEQ ID NO 360
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 360
gtggtcccca gattcatacc tgg                                                    23

<210> SEQ ID NO 361
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 361
acccttcata ggcttcatcc agg                                                    23

<210> SEQ ID NO 362
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 362
cgatctctgg caggctgctc agg                                                    23

<210> SEQ ID NO 363
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 363
cacggccctc acctactacc tgg                                                    23

<210> SEQ ID NO 364
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 364
```

-continued

```
accctgtgtc tgccttcctt agg                                              23

<210> SEQ ID NO 365
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 365
ggccaccacg cctgtcatca tgg                                              23

<210> SEQ ID NO 366
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 366
cgatgggggg ccgcagggac ggg                                              23

<210> SEQ ID NO 367
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 367
ggggcgcacc ttgccctcgc cgg                                              23

<210> SEQ ID NO 368
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 368
tcacacaggt ggtcgatggg ggg                                              23

<210> SEQ ID NO 369
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 369
aacggattct tggcatcaaa ggg                                              23

<210> SEQ ID NO 370
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 370
cggccgccgt tctccccggc agg                                              23

<210> SEQ ID NO 371
<211> LENGTH: 23
<212> TYPE: DNA
<213> ORGANISM: Artificial Sequence
```

-continued

<220> FEATURE:
<223> OTHER INFORMATION: Cypor CRISPR target sequences

<400> SEQUENCE: 371
taacagtttc atgatcaaca tgg                                              23

<210> SEQ ID NO 372
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 372
gaaccagaag ccgtgagtgg agg                                              23

<210> SEQ ID NO 373
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 373
tcctcggccc agcttggagg agg                                              23

<210> SEQ ID NO 374
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 374
atgctggaaa ggggagacca agg                                              23

<210> SEQ ID NO 375
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 375
gatgtccagg tagtaggtga ggg                                              23

<210> SEQ ID NO 376
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 376
ctggcgcagt tccacaggga cgg                                              23

<210> SEQ ID NO 377
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 377
gaagtcctgg gcattgtcgg tgg                                              23

-continued

```
<210> SEQ ID NO 378
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 378
caccttggag gatgaggcga tgg                                              23

<210> SEQ ID NO 379
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 379
aggcatgtca gcggaccctg agg                                              23

<210> SEQ ID NO 380
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 380
catcaagaaa ctgatgacca agg                                              23

<210> SEQ ID NO 381
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 381
acaagggcgt ggccaccaac tgg                                              23

<210> SEQ ID NO 382
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 382
ggagctgtac ctgagctggg tgg                                              23

<210> SEQ ID NO 383
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 383
acagagttgg ggtggacctg tgg                                              23

<210> SEQ ID NO 384
<211> LENGTH: 23
<212> TYPE: DNA
<213> ORGANISM: Artificial Sequence
<220> FEATURE:
<223> OTHER INFORMATION: Cypor CRISPR target sequences
```

-continued

```
<400> SEQUENCE: 384
cagctcacac aggtggtcga tgg                                        23

<210> SEQ ID NO 385
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 385
tgagctgggt ggtggaggcc cgg                                        23

<210> SEQ ID NO 386
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 386
gcaggtgctg gacgtagacc tgg                                        23

<210> SEQ ID NO 387
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 387
aagtcctggg cattgtcggt ggg                                        23

<210> SEQ ID NO 388
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 388
ggaactgcgc cagctcctcc cgg                                        23

<210> SEQ ID NO 389
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 389
gcttcatcca ggagcgggcc tgg                                        23

<210> SEQ ID NO 390
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 390
cacccaggat tttgcccagc tgg                                        23

<210> SEQ ID NO 391
```

-continued

```
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 391
gacaggcgtg gtggccttga agg                                                     23

<210> SEQ ID NO 392
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 392
gcgggccaag gagcctgccg ggg                                                     23

<210> SEQ ID NO 393
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 393
cgtggctgag ctcggggcca tgg                                                     23

<210> SEQ ID NO 394
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 394
ttgcctgcgt ggcaggggcc ggg                                                     23

<210> SEQ ID NO 395
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 395
ctacctgtac cgggaggagc tgg                                                     23

<210> SEQ ID NO 396
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 396
tcacctggcg agagcagttc tgg                                                     23

<210> SEQ ID NO 397
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 397
```

-continued tggcagctgg tacctgattt tgg                                                    23

<210> SEQ ID NO 398
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 398
cgtagacctg gggccaaggg tgg                                                    23

<210> SEQ ID NO 399
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 399
gtccccagat tcatacctgg agg                                                    23

<210> SEQ ID NO 400
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 400
ggatgcacgg aacatggcca ggg                                                    23

<210> SEQ ID NO 401
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 401
gggatgcacg gaacatggcc agg                                                    23

<210> SEQ ID NO 402
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 402
ggaccctgag gagtatgacc tgg                                                    23

<210> SEQ ID NO 403
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 403
ggagaaggcc acgttgagct ggg                                                    23

<210> SEQ ID NO 404
<211> LENGTH: 23
<212> TYPE: DNA

-continued

```
<213> ORGANISM: Artificial Sequence
<220> FEATURE:
<223> OTHER INFORMATION: Cypor CRISPR target sequences

<400> SEQUENCE: 404
catacctgga gggagatgtg agg                                              23

<210> SEQ ID NO 405
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 405
gctcacacag gtggtcgatg ggg                                              23

<210> SEQ ID NO 406
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 406
ggggtctccc tcaccgtagg tgg                                              23

<210> SEQ ID NO 407
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 407
gcacatcctg gccatcctgc agg                                              23

<210> SEQ ID NO 408
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 408
ttcttgttgg actcctctgc agg                                              23

<210> SEQ ID NO 409
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 409
gcccagcgca tctttgagct ggg                                              23

<210> SEQ ID NO 410
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 410
aaggtgtaca tgggggagat ggg                                              23
```

```
<210> SEQ ID NO 411
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 411
cttgccctcg ccggaggagg agg                                                     23

<210> SEQ ID NO 412
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 412
caccttgccc tcgccggagg agg                                                     23

<210> SEQ ID NO 413
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 413
ggcgcggcag cagctcacac agg                                                     23

<210> SEQ ID NO 414
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 414
cccctgccac gcaggcaagg agg                                                     23

<210> SEQ ID NO 415
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 415
gcgcagcagc tcctgctccg agg                                                     23

<210> SEQ ID NO 416
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 416
ctcctcctcc ggcgagggca agg                                                     23

<210> SEQ ID NO 417
<211> LENGTH: 23
<212> TYPE: DNA
<213> ORGANISM: Artificial Sequence
<220> FEATURE:
```

-continued

<223> OTHER INFORMATION: Cypor CRISPR target sequences

<400> SEQUENCE: 417
cgggcctggc tgcgacagca ggg                                                    23

<210> SEQ ID NO 418
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 418
gtcgcagcca ggcccgctcc tgg                                                    23

<210> SEQ ID NO 419
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 419
aagggtgcca ccccggtgcc ggg                                                    23

<210> SEQ ID NO 420
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 420
gcccaccatg atgacaggcg tgg                                                    23

<210> SEQ ID NO 421
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 421
agggtgagtg gggtcccatg ggg                                                    23

<210> SEQ ID NO 422
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 422
tggcatcaaa ggggctgggt ggg                                                    23

<210> SEQ ID NO 423
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 423
tgtcagagag agcagctttg tgg                                                    23

-continued

```
<210> SEQ ID NO 424
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 424
tctccctcca ggtatgaatc tgg                                              23

<210> SEQ ID NO 425
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 425
tgtggaaaag atgaagaaaa cgg                                              23

<210> SEQ ID NO 426
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 426
cttggcccgc agccagttgg tgg                                              23

<210> SEQ ID NO 427
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 427
tggacgtaga cctggggcca agg                                              23

<210> SEQ ID NO 428
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 428
caccacgcct gtcatcatgg tgg                                              23

<210> SEQ ID NO 429
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 429
atgaagtcct cctccaagct ggg                                              23

<210> SEQ ID NO 430
<211> LENGTH: 23
<212> TYPE: DNA
<213> ORGANISM: Artificial Sequence
<220> FEATURE:
<223> OTHER INFORMATION: Cypor CRISPR target sequences
```

-continued

<400> SEQUENCE: 430
caaccagctg ggcaaaatcc tgg                                                                                             23

<210> SEQ ID NO 431
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 431
gaaggtgttc tgcacatccc tgg                                                                                             23

<210> SEQ ID NO 432
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 432
aaccagaagc cgtgagtgga ggg                                                                                             23

<210> SEQ ID NO 433
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 433
aagccactgg cgaggagtcc agg                                                                                             23

<210> SEQ ID NO 434
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 434
aaagctgctc tctctgacag agg                                                                                             23

<210> SEQ ID NO 435
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 435
attcttggca tcaaaggggc tgg                                                                                             23

<210> SEQ ID NO 436
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 436
ctcaccctgc tgtcgcagcc agg                                                                                             23

<210> SEQ ID NO 437
<211> LENGTH: 23

```
<212> TYPE: DNA
<213> ORGANISM: Artificial Sequence
<220> FEATURE:
<223> OTHER INFORMATION: Cypor CRISPR target sequences

<400> SEQUENCE: 437
ccacgcaggc aaggaggtgg ggg                                            23

<210> SEQ ID NO 438
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 438
gctgtacctg agctgggtgg tgg                                            23

<210> SEQ ID NO 439
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 439
agccgtgagt ggagggagcg tgg                                            23

<210> SEQ ID NO 440
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 440
gggtgagtga gtggggtcac tgg                                            23

<210> SEQ ID NO 441
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 441
ggacgggcag tcctgcagga tgg                                            23

<210> SEQ ID NO 442
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 442
ctcctgctcc gagggctccg agg                                            23

<210> SEQ ID NO 443
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 443
```

-continued

```
cgcctcggac acggtggagc tgg                                              23

<210> SEQ ID NO 444
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 444
tcctcctcca agctgggccg agg                                              23

<210> SEQ ID NO 445
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 445
ttcttggcat caaaggggct ggg                                              23

<210> SEQ ID NO 446
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 446
ctctcctcgg cccagcttgg agg                                              23

<210> SEQ ID NO 447
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 447
aagctcgtac tggcgaatgc tgg                                              23

<210> SEQ ID NO 448
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 448
cgagcctcac atctccctcc agg                                              23

<210> SEQ ID NO 449
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 449
cgccctggtg gttttctgca tgg                                              23

<210> SEQ ID NO 450
<211> LENGTH: 23
<212> TYPE: DNA
<213> ORGANISM: Artificial Sequence
```

-continued

```
<220> FEATURE:
<223> OTHER INFORMATION: Cypor CRISPR target sequences

<400> SEQUENCE: 450
ctccctccac tcacggcttc tgg                                              23

<210> SEQ ID NO 451
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 451
ggtgggcccc ggcaccgggg tgg                                              23

<210> SEQ ID NO 452
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 452
tgatgtccag gtagtaggtg agg                                              23

<210> SEQ ID NO 453
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 453
tgatgccaag aatccgttcc tgg                                              23

<210> SEQ ID NO 454
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 454
ctggctgcag gagacagacg tgg                                              23

<210> SEQ ID NO 455
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 455
gggtgagtgg ggtcccatgg ggg                                              23

<210> SEQ ID NO 456
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 456
gtgcatccct gggcaggaag agg                                              23
```

<210> SEQ ID NO 457
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 457
gtacctgagc tgggtggtgg agg                                                    23

<210> SEQ ID NO 458
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 458
cgcagcagct cctgctccga ggg                                                    23

<210> SEQ ID NO 459
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 459
tacgtctgtg ggtgagtgag tgg                                                    23

<210> SEQ ID NO 460
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 460
ctcctctcct cggcccagct tgg                                                    23

<210> SEQ ID NO 461
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 461
tgagctgctg ccgcgcctgc agg                                                    23

<210> SEQ ID NO 462
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 462
tcgcctcatc ctccaaggtg agg                                                    23

<210> SEQ ID NO 463
<211> LENGTH: 23
<212> TYPE: DNA
<213> ORGANISM: Artificial Sequence
<220> FEATURE:
<223> OTHER INFORMATION: Cypor CRISPR target sequences -continued

<400> SEQUENCE: 463
gccacgcagg caaggaggtg ggg                                            23

<210> SEQ ID NO 464
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 464
tcttgttgga ctcctctgca ggg                                            23

<210> SEQ ID NO 465
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 465
ccctgtgtct gccttcctta ggg                                            23

<210> SEQ ID NO 466
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 466
atgttgatca tgaaactgtt agg                                            23

<210> SEQ ID NO 467
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 467
ctccaagctg ggccgaggag agg                                            23

<210> SEQ ID NO 468
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 468
ttggggtgga cctgtgggga ggg                                            23

<210> SEQ ID NO 469
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 469
ggccctcacc ttggaggatg agg                                            23

<210> SEQ ID NO 470

-continued

```
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 470
gcagggtgag tggggtccca tgg                                          23

<210> SEQ ID NO 471
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 471
ggcagtcctg caggatggcc agg                                          23

<210> SEQ ID NO 472
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 472
ggatggtgag tgccacagtc agg                                          23

<210> SEQ ID NO 473
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 473
gttggggtgg acctgtgggg agg                                          23

<210> SEQ ID NO 474
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 474
tgctggaaag gggagaccaa ggg                                          23

<210> SEQ ID NO 475
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 475
tggccatgca gaaaaccacc agg                                          23

<210> SEQ ID NO 476
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 476
```

-continued

```
ggcatcaaag gggctgggtg ggg                                          23

<210> SEQ ID NO 477
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 477
cagggtgagt ggggtcccat ggg                                          23

<210> SEQ ID NO 478
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 478
gcacagatgt gcacagagtt ggg                                          23

<210> SEQ ID NO 479
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 479
gcaggagctg ctgcgcaaga tgg                                          23

<210> SEQ ID NO 480
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 480
gctcacacgg ccctccccac agg                                          23

<210> SEQ ID NO 481
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 481
gcggcagcag ctcacacagg tgg                                          23

<210> SEQ ID NO 482
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 482
gatggtgagt gccacagtca ggg                                          23

<210> SEQ ID NO 483
<211> LENGTH: 23
<212> TYPE: DNA
```

-continued

```
<213> ORGANISM: Artificial Sequence
<220> FEATURE:
<223> OTHER INFORMATION: Cypor CRISPR target sequences

<400> SEQUENCE: 483
agatgtgcac agagttgggg tgg                                                23

<210> SEQ ID NO 484
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 484
gcatccctgg gcaggaagag ggg                                                23

<210> SEQ ID NO 485
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 485
gcagggacgg gcagtcctgc agg                                                23

<210> SEQ ID NO 486
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 486
ggttggtggt gactgcagcc agg                                                23

<210> SEQ ID NO 487
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 487
caccatgatg acaggcgtgg tgg                                                23

<210> SEQ ID NO 488
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 488
tggctgggta cacagccacg tgg                                                23

<210> SEQ ID NO 489
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 489
tgcctgtctc ttccctgcag agg                                                23
```

-continued

<210> SEQ ID NO 490
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 490
ggaggcccgg aggcacatcc tgg                                                            23

<210> SEQ ID NO 491
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 491
cgggaatggg tgcttcttgt tgg                                                            23

<210> SEQ ID NO 492
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 492
ctcctctgca gggaagagac agg                                                            23

<210> SEQ ID NO 493
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 493
gctgggtggt ggaggcccgg agg                                                            23

<210> SEQ ID NO 494
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 494
agcaccccct cttcctgccc agg                                                            23

<210> SEQ ID NO 495
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 495
cgtctgtggg tgagtgagtg ggg                                                            23

<210> SEQ ID NO 496
<211> LENGTH: 23
<212> TYPE: DNA
<213> ORGANISM: Artificial Sequence
<220> FEATURE:

<223> OTHER INFORMATION: Cypor CRISPR target sequences

<400> SEQUENCE: 496
atcaaagggg ctgggtgggg agg                                          23

<210> SEQ ID NO 497
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 497
tgcctgcgtg gcaggggccg ggg                                          23

<210> SEQ ID NO 498
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 498
cacagatgtg cacagagttg ggg                                          23

<210> SEQ ID NO 499
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 499
acagcaccac ccttggcccc agg                                          23

<210> SEQ ID NO 500
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 500
gggcctccac cacccagctc agg                                          23

<210> SEQ ID NO 501
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 501
cggcccctgc cacgcaggca agg                                          23

<210> SEQ ID NO 502
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 502
acgtctgtgg gtgagtgagt ggg                                          23

-continued

```
<210> SEQ ID NO 503
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 503
cacttacaat gtctgaattt tgg                                      23

<210> SEQ ID NO 504
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 504
gctgctctct ctgacagagg agg                                      23

<210> SEQ ID NO 505
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 505
acaggcgtgg tggccttgaa ggg                                      23

<210> SEQ ID NO 506
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 506 gcacccctc ttcctgccca ggg                                       23

<210> SEQ ID NO 507
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 507
tgcatccctg ggcaggaaga ggg                                      23

<210> SEQ ID NO 508
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 508
cctgtgtcca cgcaggtgtt tgg                                      23

<210> SEQ ID NO 509
<211> LENGTH: 23
<212> TYPE: DNA
<213> ORGANISM: Artificial Sequence
<220> FEATURE:
<223> OTHER INFORMATION: Cypor CRISPR target sequences
```

-continued

<400> SEQUENCE: 509
catccctggg caggaagagg ggg                                                              23

<210> SEQ ID NO 510
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 510
ctgggccgag gagaggagag ggg                                                              23

<210> SEQ ID NO 511
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 511
tctgcaggga agagacaggc agg                                                              23

<210> SEQ ID NO 512
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 512
gctgggccga ggagaggaga ggg                                                              23

<210> SEQ ID NO 513
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 513
gggagaaggc cacgttgagc tgg                                                              23

<210> SEQ ID NO 514
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 514
agctgggccg aggagaggag agg                                                              23

<210> SEQ ID NO 515
<211> LENGTH: 23
<212> TYPE: DNA
<213> ORGANISM: Artificial Sequence
<220> FEATURE:
<223> OTHER INFORMATION: Cypor CRISPR target sequences

<400> SEQUENCE: 515
cttctttttt ctttctgaag agg                                                              23

<210> SEQ ID NO 516
<211> LENGTH: 23

-continued

<212> TYPE: DNA
<213> ORGANISM: Artificial Sequence
<220> FEATURE:
<223> OTHER INFORMATION: Cypor CRISPR target sequences

<400> SEQUENCE: 516
caccccggcc cctgccacgc agg                                                                        23

<210> SEQ ID NO 517
<211> LENGTH: 80
<212> TYPE: RNA
<213> ORGANISM: Artificial Sequence
<220> FEATURE:
<223> OTHER INFORMATION: gRNA

<400> SEQUENCE: 517
guuuuagagc uagaaauagc aaguuaaaau aaggcuaguc cguuaucaac uugaaaaagu       60
ggcaccgagu cggugcuuuu                                                                            80

<210> SEQ ID NO 518
<211> LENGTH: 20
<212> TYPE: DNA
<213> ORGANISM: Artificial Sequence
<220> FEATURE:
<223> OTHER INFORMATION: oligonucleotide

<400> SEQUENCE: 518
tcgtgggggt cctgacctac                                                                            20

<210> SEQ ID NO 519
<211> LENGTH: 25
<212> TYPE: DNA
<213> ORGANISM: Artificial Sequence
<220> FEATURE:
<223> OTHER INFORMATION: oligonucleotide

<400> SEQUENCE: 519
caccgtcgtg ggggtcctga cctac                                                                      25

<210> SEQ ID NO 520
<211> LENGTH: 25
<212> TYPE: DNA
<213> ORGANISM: Artificial Sequence
<220> FEATURE:
<223> OTHER INFORMATION: oligonucleotide

<400> SEQUENCE: 520
aaacgtaggt caggacccccc acgac                                                                     25

<210> SEQ ID NO 521
<211> LENGTH: 43
<212> TYPE: RNA
<213> ORGANISM: Artificial Sequence
<220> FEATURE:
<223> OTHER INFORMATION: Hammerhead ribozyme
<220> FEATURE:
<221> NAME/KEY: misc_feature
<222> LOCATION: (1)...(6)
<223> OTHER INFORMATION: n = a, c, g, or u

<400> SEQUENCE: 521
nnnnnncuga ugaguccgug aggacgaaac gaguaagcuc guc                                                  43

<210> SEQ ID NO 522
<211> LENGTH: 68
<212> TYPE: RNA

-continued

```
<213> ORGANISM: Artificial Sequence
<220> FEATURE:
<223> OTHER INFORMATION: HDV ribozyme

<400> SEQUENCE: 522
ggccggcaug gucccagccu ccucgcuggc gccggcuggg caacaugcuu cggcauggcg        60
aaugggac                                                                 68

<210> SEQ ID NO 523
<211> LENGTH: 100
<212> TYPE: RNA
<213> ORGANISM: Artificial Sequence
<220> FEATURE:
<223> OTHER INFORMATION: Guide RNA
<220> FEATURE:
<221> NAME/KEY: misc_feature
<222> LOCATION: (1)...(20)
<223> OTHER INFORMATION: n = a, c, g, or u

<400> SEQUENCE: 523
nnnnnnnnnn nnnnnnnnnn guuuuagagc uagaaauagc aaguuaaaau aaggcuaguc        60
cguuaucaac uuuaaaaagu ggcaccgagu cggugcuuuu                             100
```

METHODS OF GENE THERAPY

This application is a § 371 application of PCT/US2019/029890, filed Apr. 30, 2019, which claims priority under 35 U.S.C. § 119(e) to U.S. Provisional Patent Application No. 62/664,930, filed Apr. 30, 2018, and U.S. Provisional Patent Application No. 62/664,932, filed Apr. 30, 2018. The foregoing applications are incorporated by reference herein.

This invention was made with government support under R01 DK048252 and R01 DK123093 awarded by the National Institutes of Health. The government has certain rights in the invention.

Incorporated herein by reference in its entirety is the Sequence Listing being concurrently submitted via EFS-Web as a text file named SeqList.txt, created Oct. 6, 2020, and having a size of 117, 222 bytes.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: SEQLIST.txt; date recorded: Apr. 29, 2019; file size: 116 KB).

FIELD OF THE INVENTION

The present invention relates to the field of gene and/or cell therapy. Specifically, compositions and methods for therapeutic gene and/or cell therapy by selecting for successfully modified cells are disclosed.

BACKGROUND OF THE INVENTION

Several publications and patent documents are cited throughout the specification in order to describe the state of the art to which this invention pertains. Each of these citations is incorporated herein by reference as though set forth in full.

Many genetic and acquired disorders affecting cells expressing cytochrome p450 (CYP) proteins are amenable to gene and/or cell therapy. Conceptually, the correction of disease-causing mutations by gene editing is the most elegant and safe method to achieve gene and/or cell therapy. Currently, recombinant adeno-associated virus (rAAV) vectors are the dominant gene therapy platform. For gene editing applications, rAAV vectors are designed to integrate therapeutic payloads into genomic loci of interest through homologous recombination. However, precise gene editing by homologous recombination in vivo has poor efficiency, typically resulting in sub-therapeutic and impermanent gene editing. Indeed, rAAV vectors remain mostly episomal and are lost with cell division. Moreover, random integration of adeno-associated viruses has been associated with liver cancer in both animals and humans, indicating a risk of harm to not only hepatocytes, but any other tissues.

One current method to address the limitations of the rAAV strategy is to directly repair the mutation(s). However in vivo gene repair with presently available methods also has poor efficiency. Another approach is to integrate a therapeutic transgene lacking its own promoter downstream of a cellular promoter into the chromosomal locus of an expressed gene. However, this method has also proven to have low efficiency.

The low efficiency of these methods can be overcome by selective amplification of cells bearing the desired gene editing event. For example, hepatocytes expressing human factor 9 properly targeted to the albumin locus can be selected by conferring resistance to drug-induced toxicity to 4-[(2-carboxyethyl)-hydroxyphosphinyl]-3-oxobutryrate (CEHPOBA), a small-molecule inhibitor of fumarylacetoacetate hydrolase, by using a short-hairpin RNA (shRNA) embedded in a microRNA within an intron to knock down tyrosine catabolic enzyme 4-OH-phenylpyruvate dioxygenase (HHPD) (Nygaard, et al. (2016) Sci. Transl. Med., 8(342):342ra79. However, use of CEHPOBA and exploitation of the tyrosine catabolic pathway for selection has limited application in vivo.

In view of the foregoing, it is clear that superior methods of gene and/or cell therapy are needed.

SUMMARY OF THE INVENTION

In accordance with the instant invention, methods of propagating and/or expanding a cell population are provided. Methods of expressing a nucleic acid of interest (e.g., a transgene) in a cell or subject are also provided (e.g., improved cell and/or gene therapy methods). In some embodiments, the method comprises inhibiting (e.g., knocking out or knocking down) one or more CYP enzymes, CTNNB1, and/or CYPOR in a cell and administering a prodrug (protoxin) to the cells. The methods may further comprise administering a nucleic acid of interest (e.g., a transgene) to the cell prior to selection with the prodrug. The administered prodrug (protoxin) is metabolized into a toxin in untreated cells but is not metabolized into a toxin in treated cells, thereby allowing for the propagating and/or expanding a desired cell population and/or expression of a nucleic acid of interest (e.g., a transgene). The steps of the method can be performed in vivo and/or in vitro. In certain embodiments, the step of inhibiting one or more CYP enzymes, CTNNB1, and/or CYPOR can be performed in vitro or in vivo. In certain embodiments, the step of administering a prodrug (protoxin) are performed by administering the prodrug (protoxin) to the subject. The step of inhibiting one or more CYP enzymes, CTNNB1, and/or CYPOR can be performed by administering an inhibitory nucleic acid molecule to the cell and/or utilizing gene editing tools such as CRISPR.

DETAILED DESCRIPTION OF THE INVENTION

Figure 1:
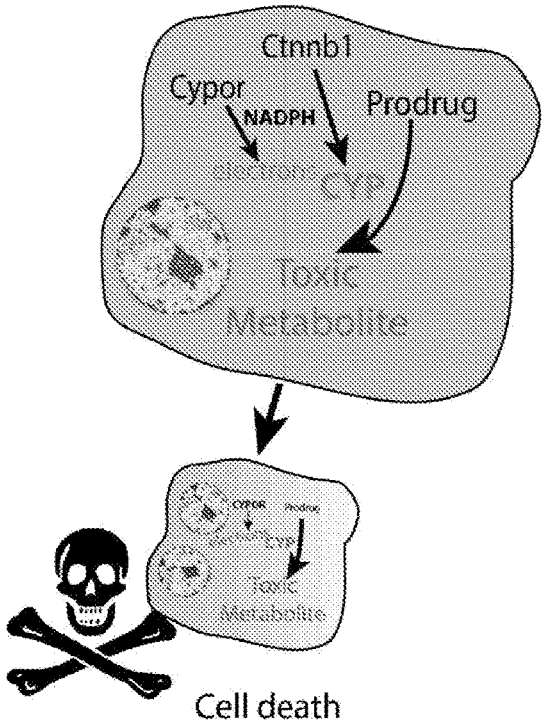
FIG. 1 provides a general schematic showing the principle of achieving drug selection by inactivating the metabolism of an inert prodrug (protoxin) into a toxic metabolite. The normal status of the cell is depicted on the left, where the prodrug (protoxin) is metabolized to a toxic metabolite. The knockdown or knockout of CYP enzymes, cytochrome P450 reductase (CYPOR or POR), or beta-catenin (Ctnnb1) protects the cells and allows them to proliferate.
Figure 1:
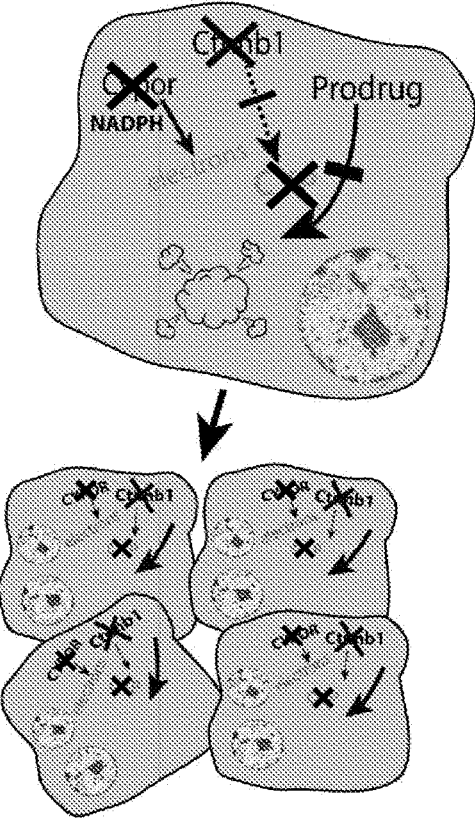

The obstacles observed with gene and/or cell therapy can be overcome through the use of: (1) methods designed to exploit and/or disrupt any gene loci required for the metabolic activity of CYP enzymes wherein the selective amplification and/or expansion of resistant cell populations through drug-induced toxicity is effected by toxins with broad application in vivo, (2) site-specific gene editing methods designed to link a desired modification to a selectable gene disruption in cis, such that selective amplification and/or cell expansion occurs only if the modification occurs at the specified site, (3) site-specific gene editing methods designed to effect a desired modification and selectable gene disruption that do not require an endonuclease enzyme to cut DNA or the use of promoters to activate gene expression such that selective amplification and/or cell expansion occurs only if the modification occurs at the specified site, (4) site-neutral gene editing methods designed to effect the desired modification and gene disruption using randomly-integrating vectors with their own endogenous promoters such that the selective amplification and/or cell expansion only occurs if integration occurs, irrespective of site, (5) methods that knock-down, knock-out, or otherwise disrupt gene loci required for the metabolic activity of CYP enzymes wherein the selective amplification and/or expansion of desired cell populations occurs without a gene editing event or modification, or (6) any combination of any of (1)-(5). The instant invention provides methods which accomplish the above.

The instant invention involves the utilization of the cytochrome p450 enzyme (CYP) system for achieving high efficiency, cell and/or tissue specific, clinically effective, higher permanence gene editing and/or therapy. The instant invention does not require a pre-existing genetic disadvantage in the cells to be edited. Rather, in some embodiments, the instant invention creates a disadvantage in un-edited cells by conferring an advantageous resistance to drug-induced toxicity to properly edited cells. This advantageous resistance can be conferred unto the cells by knocking down, knocking out, or otherwise disrupting: (1) one or more CYP genes that encode CYP enzymes, (2) the cytochrome p450 reductase (CYPOR or POR) gene, (3) the CTNNB1 (beta-catenin) gene, (4) any gene loci required for metabolic activity of CYP enzymes, or (5) any combination of any of (1)-(4). Moreover, advantageous resistance can also be conferred by disabling, disrupting, or otherwise inactivating one or more CYP enzyme, CTNNB1, and/or CYPOR directly. Upon administration of an appropriate toxin (e.g., a prodrug or protoxin), cells with advantageous resistance (i.e., lack the ability to metabolize and activate the toxin due to reduction in CYP activity) will preferentially propagate over those cells which were not edited.

In accordance with one aspect of the instant invention, methods of propagating and/or expanding a cell population are provided. In some embodiments, the method comprises inhibiting (e.g., knocking out or knocking down) one or more CYP enzymes, CTNNB1, and/or CYPOR in a cell, and administering a prodrug (protoxin) to the cells, wherein the administered prodrug (protoxin) is metabolized into a toxin in untreated cells (e.g., cells wherein CYP enzymes, CTNNB1, and/or CYPOR are not inhibited) but is not metabolized into a toxin in treated cells (e.g., cells wherein CYP enzymes, CTNNB1, and/or CYPOR are inhibited). The steps of the method can be performed in vivo and/or in vitro, including ex vivo methods (e.g., wherein cells from a subject (autologous cells) are treated in vitro and then administered back to the subject. In certain embodiments, the step of inhibiting one or more CYP enzymes, CTNNB1, and/or CYPOR can be performed in vitro or in vivo. In certain embodiments, the step of administering a prodrug (protoxin) can be performed in vitro or in vivo (e.g., the prodrug (protoxin) can be administered generally to the subject comprising the cells or administered directly to the cells).

In accordance with another aspect of the instant invention, methods of expressing a nucleic acid of interest (e.g., a transgene) in a cell are provided. In some embodiments, the method comprises inhibiting (e.g., knocking out or knocking down) one or more CYP enzymes, CTNNB1, and/or CYPOR in a cell, introducing the nucleic acid of interest (e.g., transgene) into the cell, and administering a prodrug (protoxin) to the cells, wherein the administered prodrug (protoxin) is metabolized into a toxin in untreated cells (e.g., cells wherein CYP enzymes, CTNNB1, and/or CYPOR are not inhibited) but is not metabolized into a toxin in treated cells (e.g., cells wherein CYP enzymes, CTNNB1, and/or CYPOR are inhibited). The steps of the method can be performed in vivo and/or in vitro, including ex vivo methods (e.g., wherein cells from a subject (autologous cells) are treated in vitro and then administered back to the subject. In certain embodiments, the step of inhibiting one or more CYP enzymes, CTNNB1, and/or CYPOR and/or introducing the nucleic acid of interest (e.g., transgene) can be performed in vitro or in vivo. The inhibition of the one or more CYP enzymes, CTNNB1, and/or CYPOR and introduction of the nucleic acid of interest (e.g., transgene) may be performed simultaneously or in cis such that both events occur within the same advantaged resistant cells. In certain embodiments, the step of administering a prodrug (protoxin) can be performed in vitro or in vivo (e.g., the prodrug (protoxin) can be administered generally to the subject comprising the cells or administered directly to the cells).

FIG. 1 provides a general schematic showing the principle of achieving drug selection by inactivating the metabolism of an inert prodrug into a toxic metabolite. The normal status of the cell is depicted on the left. The metabolizing enzyme is expressed in normal cells, resulting in toxicity after metabolic conversion. If the gene(s) responsible for the metabolic activity are either knocked down (e.g., siRNA or shRNA) or knocked out (e.g., targeted nuclease (e.g., CRISPR)), the toxic metabolite is not produced after administration of the toxic precursor. Knockdown or knockout cells are protected and can proliferate, whereas enzyme positive cells die. As seen in FIG. 1, the knockdown or knockout of a CYP enzymes, cytochrome P450 reductase (CYPOR or POR), or beta-catenin (Ctnnb1) can prevent the conversion of the prodrug (protoxin) such as acetaminophen to its toxic metabolite. Notably, POR donates electrons from NADPH to all CYP enzymes and, hence, is essential for their activity. In the absence of POR, all CYP enzymes are inactive. Similarly, Ctnnb1 is essential for the transcription of genes expressed in zone 3 hepatocytes, including Cyp1A2, 2E1 and 3A4. At least these CYP enzymes will be absent from Ctnnb1 inhibited cells.

The cells of the methods of the instant invention can be any cell type. In some embodiments, the cells have CYP activity. In some embodiments, the cells are hepatocytes.

The inhibition (e.g., knockout or knockdown) of one or more CYP enzymes, CTNNB1, and/or CYPOR in a cell can be performed by any method known in the art. In a particular embodiment, the inhibition is achieved by administering an inhibitor of one or more CYP enzymes, CTNNB1, and/or CYPOR to the cell. Such inhibitors are compounds which reduce the activity of the target gene and/or protein (e.g., inhibit or reduce substrate interaction) and/or reduce the expression of the target gene and/or protein. Examples of inhibitors include, without limitation, proteins, polypeptides, peptides, antibodies, small molecules, and nucleic acid molecules. Preferably, the inhibitor is a nucleic acid-based inhibitor. In some embodiments, the inhibitor is an inhibitory nucleic acid molecule, such as an antisense, siRNA, or shRNA molecule (or a nucleic acid molecule encoding the inhibitory nucleic acid molecule). In some embodiments, the inhibitor is a gene editing inhibitor such as a CRISPR based targeting of the desired gene (e.g., with a guide RNA targeting the desired gene).

CYP genes are well known in the art and include any cytochrome p450 gene. Examples of CYP genes are provided in Nelson, D. R. (Human Genomics (2009) 4:59-65; incorporated by reference herein). Examples of CYP genes include, without limitation, cytochrome p450 gene families 1 through 51. Examples of CYP genes include, without limitation, CYP1A (e.g., CYP1A1, CYP1A2), CYP1B (e.g., CYP1B1), CYP2A (e.g., CYP2A6, CYP2A7, CYP2A13), CYP2B (e.g., CYP2B6), CYP2C (e.g., CYP2C8, CYP2C9, CYP2C18, CYP2C19), CYP2D (e.g., CYP2D6), CYP2E (e.g., CYP2E1), CYP2F (e.g., CYP2F1), CYP2J (e.g., CYP2J2), CYP2R (e.g., CYP2R1), CYP2S (e.g., CYP2S1), CYP2U (e.g., CYP2U1), CYP2W (e.g., CYP2W1), CYP3A (e.g., CYP3A4, CYP3A5, CYP3A7, CYP3A43), CYP4A (e.g., CYP4A11, CYP4A22), CYP4B (e.g., CYP4B1), CYP4F (e.g., CYP4F2, CYP4F3, CYP4F8, CYP4F11, CYP4F12, CYP4F22), CYP4V (e.g., CYP4V2), CYP4X (e.g., CYP4X1), CYP4Z (e.g., CYP4Z1), CYP5A (e.g., CYP5A1) CYP7A (e.g., CYP7A1), CYP7B (e.g., CYP7B1), CYP8B (e.g., CYP8B1), CYP11A (e.g., CYP11A1), CYP11B (e.g., CYP11B1, CYP11B2), CYP17A (e.g., CYP17A1), CYP 19A (e.g., CYP19A1), CYP20 (e.g., CYP20A1), CYP21A (e.g., CYP21A2), CYP24A (e.g., CYP24A1), CYP26A (e.g., CYP26A1), CYP26B (e.g., CYP26B1), CYP26C (e.g., CYP26C1), CYP27A (e.g., CYP27A1), CYP27B (e.g., CYP27B1), CYP27C (e.g., CYP27C1), CYP39A (e.g., CYP39A1), CYP46A (e.g., CYP46A1), and CYP51A (e.g., CYP51A1). In a particular embodiment, the CYP gene is from a subfamily selected from CYP1, CYP2, or CYP3.

Cytochrome P450 reductase (CYPOR or POR; the terms have been used interchangeably herein) is an endoplasmic reticulum membrane oxidoreductase protein with FAD and FMN binding domains which allows it to donate electrons directly from NADPH to all cytochrome p450 enzymes (Iyanagi, et al., (2012) Arch. Biochem. Biophys., 528:72-89). In humans, the cytochrome P450 reductase gene is found at locus: chromosome 7, q-arm, region 1, band 1, sub-band 23 (7q11.23) (see, e.g., GenBank Accession No. NC_000007.14). Examples of nucleotide and amino acids sequences of human POR can be found, for example, at Gen Bank Gene ID: 5447 and GenBank Accession Nos. NM_000941.3 and NP 000932.3.

Catenin beta-1 (CTNNB1; also known as β-catenin) is a dual function protein involved in regulation and coordination of cell-cell adhesion and gene transcription. Examples of nucleotide and amino acids sequence of human Ctnnb1 can be found, for example, at Gen Bank Gene ID: 1499 and GenBank Accession Nos. NM_001098209.1 and NP_001091679.1.

As stated hereinabove, the genome of the cell may be edited to inactivate/inhibit one or more CYP enzymes, CTNNB1, and/or CYPOR. The genome of the cells can be edited using any method known in the art such as, without limitation: zinc finger nucleases (ZFNs), transcription activator like effector nucleases (TALENs), clustered regularly interspaced short palindromic repeats (CRISPRs), and meganucleases. In some embodiments, CRISPR is utilized. Clustered, regularly interspaced, short palindromic repeat (CRISPR)/Cas9 (e.g., from *Streptococcus pyogenes*) technology and gene editing are well known in the art (see, e.g., Shi et al. (2015) Nat. Biotechnol., 33(6):661-7; Sander et al. (2014) Nature Biotech., 32:347-355; Jinek et al. (2012) Science, 337:816-821; Cong et al. (2013) Science 339:819-823; Ran et al. (2013) Nature Protocols 8:2281-2308; Mali et al. (2013) Science 339:823-826; Sapranauskas et al. (2011) Nucleic Acids Res. 39:9275-9282; Nishimasu et al. (2014) Cell 156(5):935-49; Swarts et al. (2012) PLoS One, 7:e35888; Sternberg et al. (2014) Nature 507(7490):62-7; addgene.org/crispr/guide). The RNA-guided CRISPR/Cas9 system involves expressing Cas9 along with a guide RNA molecule (gRNA). Guidelines and computer-assisted methods for generating gRNAs are available (see, e.g, CRISPR Design Tool (crispr.mit.edu); Hsu et al. (2013) Nat. Biotechnol. 31:827-832; addgene.org/CRISPR; and CRISPR gRNA Design tool—DNA2.0 (dna20.com/eCommerce/startCas9)). When coexpressed, gRNAs bind and recruit Cas9 to a specific genomic target sequence where it mediates a double strand DNA (dsDNA) break. More than one gRNA (e.g., 2) may be administered to make multiple breaks within the target DNA. The double strand break can be repaired by non-homologous end joining (NHEJ) pathway yielding an insertion and/or deletion or, in the presence of a donor template, by homology-directed repair (HDR) pathway for replacement mutations (Overballe-Petersen et al. (2013) Proc. Natl. Acad. Sci., 110:19860-19865; Gong et al. (2005) Nat. Struct. Mol. Biol., 12:304-312). While CRISPR is described herein as utilizing Cas9, other nucleases such as Cas9 variants and homologs can be used. Other examples include, without limitation, *Streptococcus pyogenes* Cas9, Cas9 D10A, high fidelity Cas9 (Kleinstiver et al. (2016) Nature, 529:490-495; Slaymaker et al. (2016) Science, 351: 84-88), Cas9 nickase (Ran et al. (2013) Cell, 154:1380-1389), *Streptococcus pyogenes* Cas9 with altered PAM specificities (e.g., SpCas9_VQR, SpCas9_EQR, and SpCas9_VRER; Kleinstiver et al. (2015) Nature, 523:481-485), *Staphylococcus aureus* Cas9, cas12a (Cpf1) (Rusk, N., Nat. Methods (2019) 16(3):215), the CRISPR/Cpf1 system of *Acidaminococcus*, and the CRISPR/Cpf1 system of Lachnospiraceae.

The binding specificity of the CRISPR/Cas9 complex depends on two different elements. First, the binding complementarity between the targeted genomic DNA (genDNA) sequence and the complementary recognition sequence of the gRNA (e.g., ~18-22 nucleotides, particularly about 20 nucleotides). Second, the presence of a proto-spacer-adjacent motif (PAM) juxtaposed to the genDNA/gRNA complementary region (Jinek et al. (2012) Science 337:816-821; Hsu et al. (2013) Nat. Biotech., 31:827-832; Sternberg et al. (2014) Nature 507:62-67). The PAM motif for *S. Pyogenes* Cas9 has been fully characterized, and is NGG or NAG (Jinek et al. (2012) Science 337:816-821; Hsu et al. (2013) Nat. Biotech., 31:827-832). Other PAMs of other Cas9 proteins are also known (see, e.g., addgene.org/crispr/guide/#pam-table). Typically, the PAM sequence is 3' of the DNA target sequence in the genomic sequence.

The guide RNA may comprise separate nucleic acid molecules. For example, one RNA may specifically hybridize to a target sequence (crRNA) and another RNA (trans-activating crRNA (tracrRNA)) specifically hybridizes with the crRNA. Preferably, the guide RNA is a single molecule (sgRNA) which comprises a sequence which specifically hybridizes with a target sequence (crRNA; complementary sequence) and a sequence recognized by Cas9 (e.g., a tracrRNA sequence; scaffold sequence). Examples of gRNA scaffold sequences are well known in the art (e.g., 5'-GUUUUAGAGC UAGAAAUAGC AAGUUAAAAU AAGGCUAGUC CGUUAUCAAC UUGAAAAAGU GGCACCGAGU CGGUGCUUUU (SEQ ID NO: 517)). As used herein, the term "specifically hybridizes" does not mean that the nucleic acid molecule needs to be 100% complementary to the target sequence. Rather, the sequence may be at least 80%, 85%, 90%, 95%, 97%, 99%, or 100% complementary to the target sequences (e.g., the complementary between the gRNA and the genomic DNA). The greater the complementarity reduces the likelihood of undesired cleavage events at other sites of the genome. In a particular embodiment, the region of complementarity (e.g., between a guide RNA and a target sequence) is at least about 10, at least about 12, at least about 15, at least about 17, at least about 20, at least about 25, at least about 30, at least about 35, or more nucleotides. In a particular embodiment, the region of complementarity (e.g., between a guide RNA and a target sequence) is about 15 to about 25 nucleotides, about 15 to about 23 nucleotides, about 16 to about 23 nucleotides, about 17 to about 21 nucleotides, about 18 to about 22 nucleotides, or about 20 nucleotides. In a particular embodiment, the guide RNA targets a sequence or comprises a sequence (e.g., RNA version) which has at least 80%, 85%, 90%, 95%, 97%, 99%, or 100% homology or identity to one of SEQ ID NOs: 34 to 516. The sequences may be extended or shortened by 1, 2, 3, 4, or 5 nucleotides at the end of the sequence opposite from the PAM (e.g., at the 5' end). When the sequence is extended, the added nucleotides should correspond to the genomic sequence.

In some embodiments, the gRNA is a self-cleaving guide RNA (scgRNA). A self-cleaving gRNA comprises ribozymes at the 5' and 3' ends of a single guide RNA. Upon expression of a scgRNA, the self-cleaving ribozymes release the gRNA within the cell to act with Cas9. In some embodiments, the scgRNA comprises a hammerhead ribozyme at the 5' of the gRNA and a hepatitis delta virus ribozyme at the 3' end of the gRNA. In some embodiments, the scgRNA is under the control of a pol2 promoter. In some embodiments, the scgRNA is under the control of a tissue specific promoter. In some embodiments, the scgRNA is under the control of the albumin promoter.

In some embodiments, the method comprises administering at least one Cas9 (e.g., the protein and/or a nucleic acid molecule encoding Cas9) and at least one gRNA (e.g., a nucleic acid molecule encoding the gRNA) to the cell or subject. In a particular embodiment, the Cas9 is *S. pyogenes* Cas9. In a particular embodiment, the targeted PAM is in the 5'UTR, 3'UTR, promoter, or intron (e.g., first intron). The nucleic acids of the instant invention may be administered consecutively (before or after) and/or at the same time (concurrently). The nucleic acid molecules may be administered in the same composition or in separate compositions. In a particular embodiment, the nucleic acid molecules are delivered in a single vector (e.g., a viral vector or a plasmid).

As stated hereinabove, an inhibitory nucleic acid molecule, such as an antisense, siRNA, or shRNA molecule (or a nucleic acid molecule encoding the inhibitory nucleic acid molecule), may be used to inactivate/inhibit one or more CYP enzyme, CTNNB1, and/or CYPOR. When an inhibitory nucleic acid molecule (e.g., an shRNA) is delivered to a cell or subject, the inhibitory nucleic acid molecule may be administered directly or an expression vector may be used. Exemplary target sequences for inhibitory nucleic acid molecules (e.g., shRNA) include, without limitation, any one of SEQ ID NOs: 2 to 33. In some embodiments, the shRNA is embedded in a microRNA.

The administration of nucleic acid molecules into cells (including to a subject) can be achieved by any method known in the art. In some embodiments, the nucleic acid molecules are introduced into cells by infection (e.g., when a viral vector is employed). In some embodiment, the nucleic acid molecules are delivered to the cells by injection, transfection, electroporation, biolistic particle delivery system (e.g., gene gun), sonoporation (e.g., cellular sonication to increase cell permeability), magnetofection (e.g., use of magnetic field to bring particles containing nucleic acid into the target cells), hydrodynamic delivery, lipoplex delivery, polymersome delivery, polyplex delivery, dendrimer delivery, nanoparticle delivery (e.g., inorganic nanoparticles), and/or through the use of cell-penetrating peptides.

The nucleic acid molecules of the instant invention may be contained within a vector (e.g., plasmid, transposon, viral vector (e.g., adeno-associated viruses (AAVs), adenoviruses, retroviruses, and lentiviruses), etc.). In some embodiments, the desired nucleic acid sequences may be expressed from appropriate promoters within the vector including a strong promoter, a constitutive promoter, tissue or cell specific promoter (e.g., hepatocyte specific promoter), and/or a regulated promoter. Examples of promoters are well known in the art and include, but are not limited to, RNA polymerase II promoters, the T7 RNA polymerase promoter, and RNA polymerase III promoters (e.g., U6 and H1; see, e.g., Myslinski et al. (2001) Nucl. Acids Res., 29:2502-09). In some embodiments, the desired nucleic acid sequences are expressed from an endogenous promoter (e.g., a promoter within the cell).

In some embodiments, the vector is an integrating vector. In further embodiments, the integrating vector does not require an endonuclease enzyme to cut DNA or the use of promoters to activate gene expression (e.g., utilizes GeneRide™ technology (LogicBio Therapeutics, Cambridge, MA)). GeneRide™ is a gene editing strategy using homologous recombination to enable site-specific transfer of genetic material that does not require an endonuclease enzyme to cut DNA or the use of promoters to activate gene expression. In further embodiments, the methods utilize randomly-integrating vectors with their own endogenous promoters such that integration occurs randomly. In some embodiments, the invention utilizes non-integrating vectors.

In some embodiments, the vector is a viral vector, particularly a rAAV vector. In some embodiments, the vector is a plasmid DNA vector. In some embodiments, the invention utilizes synthetic oligonucleotide vectors. In some embodiments, the invention utilizes retroviral vectors such as vectors based on foamy virus, oncovirus, and/or lentivirus. In another embodiment, the vector is based on adenoviruses. In another embodiment, the vector is based on AAV. In another embodiment, the vector is based on envelope protein pseudotyping of viral vectors. In another embodiment, the vector is based on replication-competent vectors and cis and trans-acting elements. In another embodiment, the vector is based on Herpes Simplex Virus.

In some embodiments, the prodrug (protoxin) administered to the cells is a compound (e.g., a small molecule) which is metabolized by CYP activity or an activity dependent on CYP activity. The toxicity of the prodrug (protoxin) to be administered to the cells can be tested on the cells to determine whether the toxin metabolite is sufficiently toxic such that an advantageous resistance can be achieved in edited cells. In some embodiment, the lethality of the toxin can be measured, wherein a toxin which causes cellular death or apoptosis to untreated cells is sufficiently toxic such that an advantageous resistance can be achieved in edited cells. In some embodiment, biomarkers within the cells can be measured to determine if the toxin is sufficiently toxic. For example, with regard to hepatocytes, a toxin may be determined to be sufficiently toxic if elevated levels of certain liver enzymes are detected including, but not limited to: alanine aminotransferase (ALT), aspartate transaminase (AST), alkaline phosphatase (ALP), or gamma-glutamyl transpeptidase (GGT). Increased expression of one or more of these liver enzymes is known to be indicative of hepatotoxicity, wherein the presence of at least mild to moderate hepatotoxicity evidences the necessary toxicity. Moreover, dosage guidelines to achieve mild to moderate hepatotoxicity are known in the art (see, e.g., Jaeschke, H. (2015) Dig. Dis., 33:464-471; Arafa, et al. (2018) Toxicol. Appl. Pharmacol., 346:37-44; Calvo, et al. (2017) Invest New Drugs, 36(3):476-486; Fashe et al. (2015) Chem. Res. Toxicol., 28:702-710; Huttunen et al. (2008) Curr. Med. Chem., 15:2346-2365; Maruyama et al. (1995) Dig. Dis. Sci., 40:2602-2607; McEneny-King et al. (2017) Bioorg. Med. Chem. Lett., 27:2443-2449).

Hepatotoxicity may be graded using the 5-point scale developed by the Drug-Induced Liver Injury Network (DILIN) (see, e.g., Fontana, et al. (2009) Drug Safety, 32:55-68). Mild hepatoxicity (or 1+) is defined as: raised serum aminotransferase or alkaline phosphatase levels or both, but total serum bilirubin is less than <2.5 mg/dL and coagulopathy is detected (INR<1.5). Moderate hepatoxicity (or 2+) is defined as: raised serum aminotransferase or alkaline phosphatase levels or both and a total serum bilirubin level of greater than or equal to 2.5 mg/dL or coagulopathy (IND≥1.5) without hyperbilirubinemia. Moderate to severe hepatoxicity (or 3+) is defined as: raised serum aminotransferase or alkaline phosphatase levels and total serum bilirubin level of ≥2.5 mg/dL and hospitalization (or preexisting hospitalization is prolonged) because of the drug induced liver injury. Severe hepatoxicity (or 4+) is defined as: raised serum aminotransferase or alkaline phosphatase levels and serum bilirubin of ≥2.5 mg/dL and at least one of the following: (a) prolonged jaundice and symptoms beyond three (3) months, (b) signs of hepatic decompensation (INR≥1.5, ascites, encephalopathy), or (c) other organ failure believed to be related to drug induced liver injury.

As explained hereinabove, the prodrug (protoxin) may be administered directly to the subject. Thus, the invention provides for methods of administering an effective dosage of a prodrug (protoxin) to human beings wherein an elevated or abnormal liver function test from the blood showing mild to moderate hepatotoxicity indicates sufficient dosage to amplify selected or edited cells. In some embodiments, dosage of the acetaminophen sufficient to induce selective toxicity in adults is: (1) 6 grams/day acetaminophen, on consecutive days, or (2) greater than 10 grams acetaminophen as a single dose.

As used herein, a CYP dependent toxin refers to a prodrug (protoxin) whose toxicity depends on activation by cytochrome p450 metabolism involving a CYP enzyme, a Cypor (POR) protein or both. Many CYP dependent toxins are metabolically activated by cytochrome p450 metabolism (see generally Jaeschke, H. (2015) Dig. Dis., 33:464-471; Huttunen et al. (2008) Curr. Med. Chem., 15:2346-2365). Often the parental compound is inert and non-toxic (e.g., a prodrug), but its metabolite(s) generated by Cyp mediated enzymatic conversion are toxic, especially hepatotoxic. For example, acetaminophen is metabolized to the hepatotoxic compound N-acetyl-p-benzoquinone imine (NAPQI) by three POR dependent CYP enzymes (CYP1A2, CYP2E1, and CYP3A4). In some embodiments, Cyp dependent toxins are used for in vivo selection of gene modified hepatocytes or other modified cells, in which the Cyp activity responsible for producing the toxic metabolite has been inactivated. Examples of CYP dependent toxins are provided in Table 1.

| Drug | Metabolizing CYP |
| --- | --- |
| Acetaminophen | CYP2E1, CYP1A2, CYP3A4, CYP2D6 |
| Retrorsine | CYP3A4 |
| Cyclophosphamide | CYP2B6, CYP2C9, CYP3A4 |
| Tamoxifen | CYP3A4 |
| Ketoconazole | CYP3A4 |
| Tramadol | CYP2D6 |
| Tacrine | CYP1A2 |
| Lasiocarpine | CYP3A4 |
| Senkirkin | CYP3A4 |
| Dascarbazine | CYP1A1, CYP1A2, CYP2E1 |
| Tegafur | CYP2A6, CYP1A2, CYP2C8 |

Table 1: CYP dependent toxins (see, e.g., Jaeschke, H. (2015) Dig. Dis., 33:464-471; Arafa, et al. (2018) Toxicol. Appl. Pharmacol., 346:37-44; Calvo, et al. (2017) Invest New Drugs, 36(3):476-486; Fashe et al. (2015) Chem. Res. Toxicol., 28:702-710; Huttunen et al. (2008) Curr. Med. Chem., 15:2346-2365; Maruyama et al. (1995) Dig. Dis. Sci., 40:2602-2607; McEneny-King et al. (2017) Bioorg. Med. Chem. Lett., 27:2443-2449; Utkarsh, et al. (2016) Chem. Biol. Interact., 255:12-22).

In one aspect, the CYP dependent toxin may include acetaminophen (APAP) as the prodrug that is converted to the active drug by any of: CYP2E1, CYP1A2, CYPA4, or CYP2D6. In another aspect, the CYP dependent toxin may include retrosine as the prodrug that is converted to the active drug by CYP3A4. In another aspect, the CYP dependent toxin may include tangretin. In another aspect, the CYP dependent toxin may include cyclopohsphamide as the prodrug that is converted to the active drug phosphoramide mustard by hydroxylation facilitated by any of: CYP2B6, CYP2C9, or CYP3A4. In another aspect, the CYP dependent toxin may include ifosfamide as the prodrug that is converted to the active drug ifosfamide mustard by hydroxylation. In another aspect, the CYP dependent toxin may include trofosfamide as the prodrug that is converted to the active drug trofosfamide mustard by hydroxylation. In another aspect, the CYP dependent toxin may include pradefovir as the prodrug that is converted to the active drug PMEA-triphosphate by hydroxylation. In another aspect, the CYP dependent toxin may include MB07133 as the prodrug that is converted to the active drug araC-triphosphate by hydroxylation. In another aspect, the CYP dependent toxin may include MB07811 as the prodrug that is converted to the active drug MB07344 by hydroxylation. In another aspect, the CYP dependent toxin may include buparvaquone hydroxyimine as the prodrug that is converted to the active drug buparvaquone mustard by oxidation. In another aspect, the CYP dependent toxin may include nabumetone hydroxyimine as the prodrug that is converted to the active drug nabumetone by oxidation. In another aspect, the CYP dependent toxin may include DB289 as the prodrug that is converted to the active drug furamidine (DB75) mustard by 0-demethylation reduction. In another aspect, the CYP dependent toxin may include sibrafiban as the prodrug that is converted to the active drug Ro 48-3888 mustard by reduction. In another aspect, the CYP dependent toxin may include ximelagatran as the prodrug that is converted to the active drug melagartan by reduction. In another aspect, the CYP dependent toxin may include guanoxabenz as the prodrug that is converted to the active drug guanabenz by reduction. In another aspect, the CYP dependent toxin may include AQ4N as the prodrug that is converted to the active drug AQ4 by reduction. In another aspect, the CYP dependent toxin may include dacarbazine ("DTIC") as the prodrug that is converted to the active drug MTIC by hydroxylation. In another aspect, the CYP dependent toxin may include tegafur as the produg that is converted to the active drug 5-FU by hydroxylation. In another aspect, the CYP Dependent Toxin may include 4-ipomeanol as the prodrug that is converted to the active drug by oxidation or epoxidation. In another aspect, the CYP dependent toxin may include DDMX ("PNU-152243") as the prodrug that is converted to the active drug PNU-159682 by cyclization. In another aspect, the CYP dependent toxin may include tamoxifen as the prodrug that is converted to the active drug 4-hydroxy-tamoxifen by hydroxylation facilitated by CYP3A4. In another aspect, the CYP dependent toxin may include tamoxifen as the prodrug that is converted to the active drug N-Desmethyl-tamoxifen by N-demethylation. In another aspect, the CYP dependent toxin may include tamoxifen as the prodrug that is converted to the active drug endoxifen by hydroxylation or N-demethylation. In another aspect, the CYP dependent toxin may include ketoconazole as a prodrug that is converted to an active drug by CYP3A4. In another aspect, the CYP dependent toxin may include tramadol as a prodrug that is converted to an active drug by CYP2D6. In another aspect, the CYP dependent toxin may include tacrine as a prodrug that is converted to an active drug by CYP1A2. In another aspect, the CYP dependent toxin may include Lasiocarpine as a prodrug that is converted to an active drug by CYP3A4. In another aspect, the CYP dependent toxin may include Senkirkin as a prodrug that is converted to an active drug by CYP3A4. In another aspect, the CYP dependent toxin may include dascarbazine as a prodrug that is converted to an active drug by any of: CYP1A1, CYP1A2, or CYP2C8. In another aspect, the CYP dependent toxin may include tegafur as a prodrug that is converted to an active drug by any of: CYP2A6, CYP1A2, or CYP2C8. In another aspect, the CYP dependent toxin may include clopidogrel as the prodrug that is converted to the active drug R-130964) by oxidation. In another aspect, the CYP dependent toxin may include V-PYRRO/NO as the prodrug that is converted to the active drug PYRRO/NO by oxidation or epoxidation. In another aspect, the CYP dependent toxin may include V-PROLI/NO as the prodrug that is converted to the active drug PROLO/NO by oxidation or epoxidation.

In some embodiments, the methods of the instant invention provide a method for selectively amplifying and/or expanding a population of cells comprising the steps of:
  a) administering a donor molecule comprising:
    i) a gRNA (e.g., a scgRNA), wherein the gRNA sequence combines with a cas9 nuclease, resulting in an active, site-nuclease designed to cut, knock down, knock out, and/or otherwise disrupt a CYP enzyme (s), the Cypor gene, or the Ctnnb1 gene;
    ii) a polymerase II promoter (e.g., a cell and/or tissue specific promoter);
    iii) a transgene (optional);
    iv) a cell and/or tissue specific Homology Arm sequence designed to facilitate, promote, or otherwise enable homologous integration into a desired recipient cell locus;
  b) administering a cas9 nuclease (e.g., protein or nucleic acid encoding Cas9) wherein the cas9 nuclease combines with a gRNA resulting in an active, site-nuclease designed to cut, knock down, knock out, and/or otherwise disrupt the a CYP enzyme(s), the Cypor gene, or the Ctnnb1 gene; and
  c) administering a prodrug (protoxin) (e.g., a CYP dependent toxin).

A scgRNA donor molecule allows expression of functional gRNA (capable of binding to cas9). The expression of the scgRNA may be limited to specific cells and/or tissue types (e.g., those that have undergone a desired gene-editing event). In a particular embodiment, cell-type specific promoters used by mammalian cells use RNA Polymerase II (Pol2) promoters. It is also known in the art that transcription driven by these promoters does not allow for proper processing of cas9 gRNA. It is also known in the art that only recipient cells that have undergone homologous recombination of a DNA donor molecule with an embedded Pol2 promoter sequence will transcribe the DNA donor molecular sequence, including the gRNA and any transgenes the DNA donor molecule may or may not contain. Conversely, it is known in the art that random integration of said homologous DNA donor molecule will not yield functional gsRNA or transgene expression. By embedding a gRNA sequence into a DNA donor molecule with Homology Arms embedded both upstream and downstream from the gRNA sequence, cell and/or tissue specific homologous recombination and integration of the DNA donor molecule into the recipient cell genome are facilitated. Further, by embedding a gRNA sequence into a DNA donor molecule wherein one or more ribozyme sequences are embedded upstream from the gRNA sequence ("left ribozyme") and one or more ribozyme sequences are embedded downstream from the gRNA sequence ("right ribozyme"), an unspliced Pol2 RNA transcript containing gRNA sequence is properly processed by the combined cleaving by the left ribozyme and the right ribozyme. Thus, the non-random, simultaneous co-expression of functional gRNA and transgenes targeted to specific cell and/or tissue types is made possible by a scgRNA molecule.

In some embodiments of the invention, the gRNA sequence is embedded into an intron of the transgene. In some embodiments, a rAAV vector is utilized. In other embodiments, a pX330 vector is utilized. In some embodiments, the homologous integration is facilitated using GeneRide™ technology wherein both transgene and selection cassette lack their own promoter; after homologous recombination into the target locus both the transgene and the CYP toxin selection cassette are expressed by a cellular promoter; only targeted integrations are selected. In further embodiments, the integration is facilitated using a randomly-integrating vector. In some embodiments, the homologous integration is facilitated using randomly-integrating vectors wherein both transgene and selection cassette have their own promoter(s); after random integration into the cellular chromosome, both the transgene and the CYP Toxin selection cassette are expressed; any chromosomal integration can be selected. In some embodiments, the gRNA sequence is designed to combined with a cas9 nuclease resulting in an active, site-specific nuclease that cuts, knocks down, knocks out, and/or otherwise disrupts individual CYP enzymes. In some embodiments, the gRNA sequence is designed to combined with a cas9 nuclease resulting in an active, site-specific nuclease that cuts, knocks down, knocks out, and/or otherwise disrupts the transcription factor Ctnnb1 (beta-catenin) that is required for the expression of CYP enzymes.

In one aspect, the disclosure provides a scgRNA donor molecule sequence (and all conservatively modified variants thereof) encoding: (a) corresponding inverted terminal repeats ("ITRs") to aid in concatemer formation set out in residues 1 to 45, and 4,406 to 4,550 of SEQ ID NO: 1, (b) corresponding mouse albumin Homology Arms as set out in residues 212 to 1,516 and 2,978 to 3,012 of SEQ ID NO: 1, (c) a RNA Polymerase II promoter sequence as set out in residues 1,517 to 1582 of SEQ Id NO: 1, (d) an example of a human Factor IX sequence as set out in residues 1,589 to 2,971 of SEQ ID NO: 1, (e) an example of a hammerhead ribozyme sequence as set out in residues 3,026 to 3068 of SEQ ID NO: 1, (f) an example of a gRNA wherein the gRNA comprises a DNA targeting segment complementary to the human POR gene as set out in residues 3,067 to 3,088 of SEQ ID NO: 1, and (g) an example of a hepatitis delta virus ribozyme as set out in residues 3,089 to 3,236 of SEQ ID NO: 1. In some embodiments, the Cypor Human Factor 9 GeneRide™ is included in a plasmid as a rAAV vector. In one embodiment, elements (e) and (g) cleave the unspliced Pol2 promoter generated RNA transcript thereby releasing the properly processed gRNA. In a non-limiting example, the 3'-terminus of element (e)'s sequence is optimally located immediately upstream (5') from the 5'-terminus of element (f), with no spacing, and the 5'-terminus of element (g) is optimally located immediately downstream (3') from the 3'-terminus of element (f), with no spacing. In some embodiments, elements (e) and (g) are not located immediately upstream and downstream respectively from element (f) but, may be located as far as 100 base pairs or more (e.g., at least 50, at least 70, or at least 100 base pairs) upstream in the case of element (e), and may be located as far as 100 base pairs or more (e.g., at least 50, at least 70, or at least 100 base pairs) downstream in the case of element (g), from element (f) respectively. In some embodiments, element (f) comprises a sequence complementary to the human POR gene as set out in one of SEQ ID NOs: 34-516.

In some embodiments, the invention provides a method for selectively amplifying and/or expanding a population of cells comprising the steps of:
a) administering a donor molecule comprising:
i) a polymerase III promoter (e.g., a U6 promoter sequence);
ii) a gRNA wherein the gRNA sequence combines with a cas9 nuclease, resulting in an active, site-nuclease designed to cut, knock down, knock out, and/or otherwise disrupt a CYP enzyme(s) or the Cypor Gene;
iii) promoter;
iv) SpCAS9 sequence wherein the cas9 nuclease expressed will combine with a gsRNA of element (b) resulting in an active, site-nuclease designed to cut, knock down, knock out, and/or otherwise disrupt CYP enzyme(s), the Cypor gene or Ctnnb1; and
b) administering a prodrug (protoxin) (e.g., a CYP dependent toxin).
In one aspect, the gRNA of element ii) comprises complementary to the human POR gene as set out in one of SEQ ID NOs: 34-516. In some embodiments, a pX330 plasmid vector is utilized. In some embodiments, homologous integration is facilitated using GeneRide™ technology wherein both transgene and selection cassette lack their own promoter; after homologous recombination into the target locus both the transgene and the CYP toxin selection cassette are expressed by a cellular promoter; only targeted integrations are selected. In further embodiments, the homologous integration is facilitated using randomly-integrating vectors wherein both transgene and selection have their own promoter(s); after random integration into the cellular chromosome, both the transgene and the Cypor selection cassette are expressed; any chromosomal integration can be selected.

In some embodiments, the instant invention provides methods for selectively amplifying and/or expanding a population of cells comprising the steps of:
a) administering a donor molecule comprising:
i) a polymerase III promoter (e.g., a U6 promoter sequence);
ii) a lentiviral-construct, shRNAmir backbone wherein the shRNA embedded in the microRNA comprises a sequence homologous to the Cypor gene; and
b) administering a prodrug (protoxin) (e.g., a CYP dependent toxin).
In some aspects, the shRNA of element ii) comprises sequence complementary to the human POR gene as set out in one of SEQ ID NOs: 2-33. In some embodiments, a rAAV vector is utilized. In other embodiments, a pX330 vector is utilized. In some embodiments, the homologous integration is facilitated using GeneRide™ technology wherein both transgene and selection cassette lack their own promoter; after homologous recombination into the target locus both the transgene and the CYP Toxin selection cassette are expressed by a cellular promoter; only targeted integrations are selected. In further embodiments, the integration is facilitated using a randomly-integrating vector. In some embodiments, the homologous integration is facilitated using randomly-integrating vectors wherein both transgene and selection cassette have their own promoter(s); after random integration into the cellular chromosome, both the transgene and the CYP toxin selection cassette are expressed; any chromosomal integration can be selected.

In some embodiments, the method comprises administering an mRNA-based donor molecule to the cells. For example, the RNA molecule may comprise a gRNA and an mRNA encoding Cas9.

In accordance with another aspect of the instant invention, methods of treating, inhibiting, and/or preventing a disease or disorder in a subject are provided. In a particular embodiment, the method comprises performing the methods of the instant invention wherein the transgene is therapeutic (e.g., encodes a therapeutic protein) for the disease or disorder to be treated. In a particular embodiment, the method comprises administering the prodrug (protoxin) to the subject. This method can be used in any system where gene-edited cells can grow in vivo. Examples of target tissues include, without limitation: the liver (e.g., hepatocytes and/or bile ducts), hematopoietic system (e.g., stem cells, T-cells, and/or progenitors), skin (e.g., dermal and/or hair-follicle stem cells), kidney (e.g., tubular epithelium), intestinal tract (e.g., stem cells), lung, and pancreas.

In some embodiments, the disease or disorder to be treated is liver disease. Examples of liver disease include, without limitation, cirrhosis, fibrosis, hepatocellular carcinoma (HCC), and hepatic infection. In some embodiments, the disease or disorder to be treated is selected from the group of genetic liver disorders including Crigler-Najjar syndrome (types 1 and 2), familial hypercholesterolemia, maple syrup urine disease, progressive familial intrahepatic cholestasis, phenylketonuria, tyrosinemia, mucopolysaccharidosis VII, alpha-1 antitrypsin (AAT) deficiency, ornithine transcarbamylase (OTC) deficiency, Wilson's disease, glycogen storage diseases, von Gierke's disease, Pompe's disease, hyperbilirubinema, acute intermittent porphyria (AIP), and citrullinemia type 1. In some embodiments, the disease or disorder to be treated is selected from the group of hemophilia A, hemophilia B, and oxalosis. In some embodiments, the disease or disorder to be treated is hepatitis B or hepatitis C. In some embodiments, the disease or disorder to be treated is selected from the group of hepatomas, cholangiocarcinomas, metastatic tumors of the liver, and extrahepatic tumors. In some embodiments, the disease or disorder to be treated is selected from the group of acute liver failure, allograft rejection, and xenograft rejection.

The components as described herein will generally be administered to a subject as a pharmaceutical preparation. The term "patient" or "subject" as used herein refers to human or animal subjects. The components of the instant invention may be employed therapeutically, under the guidance of a physician for the treatment of the indicated disease or disorder.

The pharmaceutical preparation comprising the components of the invention may be conveniently formulated for administration with an acceptable medium (e.g., pharmaceutically acceptable carrier) such as water, buffered saline, ethanol, polyol (for example, glycerol, propylene glycol, liquid polyethylene glycol and the like), dimethyl sulfoxide (DMSO), oils, detergents, suspending agents or suitable mixtures thereof. The concentration of the agents in the chosen medium may be varied and the medium may be chosen based on the desired route of administration of the pharmaceutical preparation. Except insofar as any conventional media or agent is incompatible with the agents to be administered, its use in the pharmaceutical preparation is contemplated.

Selection of a suitable pharmaceutical preparation depends upon the method of administration chosen. For example, the components of the invention may be administered by direct injection into any desired tissue (e.g., liver) or into the surrounding area. In this instance, a pharmaceutical preparation comprises the components dispersed in a medium that is compatible with blood or the target tissue.

The therapy may be, for example, administered parenterally, by injection into the blood stream (e.g., intravenous), orally, or by subcutaneous, intramuscular or intraperitoneal injection. In a particular embodiment, the therapy is administered by direct injection (e.g., into the tissue to be treated) or orally. Pharmaceutical preparations for injection are known in the art. If injection is selected as a method for administering the therapy, steps must be taken to ensure that sufficient amounts of the molecules reach their target cells to exert a biological effect.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In the preparation of an oral dosage form, any of the usual pharmaceutical media may be employed, such as, for example, water, glycols, oils, alcohols, flavoring agents, preservatives, coloring agents and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Injectable suspensions may be prepared, in which case appropriate liquid carriers, suspending agents and the like may be employed.

A pharmaceutical preparation of the invention may be formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art. Dosage units may be proportionately increased or decreased based on the weight of the patient. Appropriate concentrations for alleviation of a particular pathological condition may be determined by dosage concentration curve calculations, as known in the art.

The methods of the instant invention may further comprise monitoring the disease or disorder in the subject after administration of the composition(s) of the instant invention to monitor the efficacy of the method.

In accordance with another aspect of the instant invention, methods of expressing a gRNA are provided. The methods comprise expressing a self-cleaving guide RNA (scgRNA) under the control of a pol2 promoter (e.g., a tissue or cell specific pol2 promoter). A self-cleaving gRNA comprises ribozymes at the 5' and 3' ends of a single guide RNA. Upon expression of a scgRNA, the self-cleaving ribozymes release the gRNA within the cell to act with Cas9. In some embodiments, the scgRNA comprises a hammerhead ribozyme at the 5' of the gRNA and a hepatitis delta virus ribozyme at the 3' end of the gRNA. The expression of scgRNA can used with any gene editing event (e.g., homologous recombination). In a particular embodiment, the scgRNA is used with the gene editing described herein (e.g., to inhibit one or more CYP enzymes, CTNNB1, and/or CYPOR in a cell). In a particular embodiment, the scgRNA is used with the gene editing described in Example 3 (e.g., to inhibit phenylpyruvate dioxygenase (Hpd) or homogentisic acid dioxygenase (Hgd), particularly in a fumarylacetoacetate hydrolase (Fah$^{-/-}$) background). Vectors comprising an scgRNA under the control of a pol2 promoter (e.g., a tissue or cell specific pol2 promoter) are also encompassed by the instant invention.

Definitions

The following definitions are provided to facilitate an understanding of the present invention:

The singular forms "a," "an," and "the" include plural referents unless the context clearly dictates otherwise. Any reference to "or" herein is intended to encompass "and/or" unless the context clearly dictates otherwise.

"Pharmaceutically acceptable" indicates approval by a regulatory agency of the Federal or a state government or listed in the U.S. Pharmacopeia or other generally recognized pharmacopeia for use in animals, and more particularly in humans.

A "carrier" refers to, for example, a diluent, adjuvant, preservative (e.g., Thimersol, benzyl alcohol), anti-oxidant (e.g., ascorbic acid, sodium metabisulfite), solubilizer (e.g., Tween® 80, Polysorbate 80), emulsifier, buffer (e.g., Tris HCl, acetate, phosphate), antimicrobial, bulking substance (e.g., lactose, mannitol), excipient, auxiliary agent or vehicle with which an active agent of the present invention is administered. Pharmaceutically acceptable carriers can be sterile liquids, such as water and oils, including those of petroleum, animal, vegetable or synthetic origin. Water or aqueous saline solutions and aqueous dextrose and glycerol solutions are preferably employed as carriers, particularly for injectable solutions. Suitable pharmaceutical carriers are described in Remington: The Science and Practice of Pharmacy, (Lippincott, Williams and Wilkins); Liberman, et al., Eds., Pharmaceutical Dosage Forms, Marcel Decker, New York, N.Y.; and Rowe, et al., Eds., Handbook of Pharmaceutical Excipients, Pharmaceutical Pr.

The term "treat" as used herein refers to any type of treatment that imparts a benefit to a patient afflicted with a disease, including improvement in the condition of the patient (e.g., in one or more symptoms), delay in the progression of the condition, etc.

As used herein, the term "prevent" refers to the prophylactic treatment of a subject who is at risk of developing a condition resulting in a decrease in the probability that the subject will develop the condition.

A "therapeutically effective amount" of a compound or a pharmaceutical composition refers to an amount effective to prevent, inhibit, or treat a particular disorder or disease and/or the symptoms thereof.

As used herein, the term "subject" refers to an animal, particularly a mammal, particularly a human.

The term "isolated" refers to the separation of a compound from other components present during its production. "Isolated" is not meant to exclude artificial or synthetic mixtures with other compounds or materials, or the presence of impurities that do not substantially interfere with the fundamental activity, and that may be present, for example, due to incomplete purification, or the addition of stabilizers.

The term "oligonucleotide," as used herein, includes a nucleic acid molecule comprised of two or more ribo- and/or deoxyribonucleotides, preferably more than three. The exact size of the oligonucleotide will depend on various factors and on the particular application and use of the oligonucleotide.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

The term "vector" refers to a carrier nucleic acid molecule (e.g., RNA or DNA) into which a nucleic acid sequence can be inserted, e.g., for introduction into a host cell where it may be expressed and/or replicated. A vector may be either RNA or DNA and may be single or double stranded. A vector may be used as a vehicle for delivering exogenous material into a recipient cell via transformation, transfection, transduction or any other mode cell penetrance. An "expression vector" is a specialized vector that contains a gene or nucleic acid sequence with the necessary operably linked regulatory regions needed for expression in a host cell (e.g., promoters, enhancers, translational start signals, polyadenylation signals, terminators, and the like). The term "operably linked" means that the regulatory sequences necessary for expression of a coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

As used herein, the term "small molecule" refers to a substance or compound that has a relatively low molecular weight (e.g., less than 4,000, less than 2,000, particularly less than 1 kDa or 800 Da). Typically, small molecules are organic, but are not proteins, polypeptides, amino acids, or nucleic acids.

The phrase "small, interfering RNA (siRNA)" refers to a short (typically less than 30 nucleotides long, particularly 12-30 or 20-25 nucleotides in length) double stranded RNA molecule. Typically, the siRNA modulates the expression of a gene to which the siRNA is targeted. Methods of identifying and synthesizing siRNA molecules are known in the art (see, e.g., Ausubel et al., Current Protocols in Molecular Biology, John Wiley and Sons, Inc). Short hairpin RNA molecules (shRNA) typically consist of short complementary sequences (e.g., an siRNA) separated by a small loop sequence (e.g., 6-15 nucleotides, particularly 7-10 nucleotides) wherein one of the sequences is complimentary to the gene target. shRNA molecules are typically processed into an siRNA within the cell by endonucleases. Exemplary modifications to siRNA molecules are provided in U.S. Application Publication No. 20050032733. For example, siRNA and shRNA molecules may be modified with nuclease resistant modifications (e.g., phosphorothioates, locked nucleic acids (LNA), 2'-O-methyl modifications, or morpholino linkages). Expression vectors for the expression of siRNA or shRNA molecules may employ a strong promoter which may be constitutive or regulated.

"Antisense nucleic acid molecules" or "antisense oligo-nucleotides" include nucleic acid molecules (e.g., single stranded molecules) which are targeted (complementary) to a chosen sequence (e.g., to translation initiation sites and/or splice sites) to inhibit the expression of a protein of interest. Such antisense molecules are typically between about 15 and about 50 nucleotides in length, more particularly between about 15 and about 30 nucleotides, and often span the translational start site of mRNA molecules. Antisense constructs may also be generated which contain the entire sequence of the target nucleic acid molecule in reverse orientation. Antisense oligonucleotides targeted to any known nucleotide sequence can be prepared by oligonucle-otide synthesis according to standard methods. Antisense oligonucleotides may be modified as described above to comprise nuclease resistant modifications.

As used herein, "downstream" means a genetic locus or sequence position that is located closer the 3'-terminus in relation to the reference locus, wherein the oligonucleotide sequence begins with the 5'-terminus and runs "5' to 3'" until ending at the 3'-terminus.

As used herein, "donor molecule" means an exogenous molecule wherein said molecule is designed to cause an effect on a recipient cell.

As used herein "embedded" means the inclusion of cer-tain desired oligonucleotide sequence within a larger syn-thetic oligonucleotide, forming a single molecule, wherein said molecule may or may not have additional activity or purpose beyond that of the embedded sequence.

As used herein, "homology arms" means target sequence with homology to a desired gene locus designed to promote, facilitate, and enable homologous integration of a donor molecule into a recipient cell genome.

As used herein, "integrating vector" means a vector that delivers donor molecules, transgenes, or other exogenous DNA or RNA, which are integrated into a recipient cell chromosome or genome.

As used herein, "knockout" means a technique by which an organism's gene is made inoperative.

As used herein, "knockdown" means a technique by which the expression of an organism's gene is reduced.

As used herein, "prodrug" means any compound that when administered to a biological system generates the drug substance, i.e., active ingredient, as a result of spontaneous chemical reaction(s), enzyme catalyzed chemical reaction (s), photolysis, and/or metabolic chemical reaction(s). A prodrug is, thus, a covalently modified analog or latent form of a compound with either therapeutic or toxic activity (e.g., a protoxin).

"Linker" refers to a chemical moiety comprising a chain of atoms that covalently attach at least two compounds. The linker can be linked to any synthetically feasible position of the compounds, but preferably in such a manner as to avoid blocking the compounds desired activity. Linkers are gen-erally known in the art. In a particular embodiment, the linker may contain from 1 to about 50 atoms, from 1 to about 10 atoms, or from about 1 to about 5 atoms.

As used herein, "shRNAmir" means a microRNA embed-ded shRNA molecule.

As used herein, "non-integrating vector" means a vector that delivers donor molecules, transgenes, or other exog-enous DNA or RNA wherein said donor molecules remain episomal and/or are not integrated into a recipient cell chromosome or genome.

As used herein, "synthetic oligonucleotide" means an oligonucleotide made by man, and not isolated from an existing natural source.

As used herein, "target sequence" means a DNA poly-nucleotide that comprises a "target site" or "target sequence." The terms "target site," or "target sequence," are used interchangeably herein to refer to a nucleic acid sequence present in a target DNA to which a DNA-targeting segment of a vector will bind, provided sufficient conditions for binding exist. Suitable DNA/RNA binding conditions include physiological conditions normally present in a cell. Other suitable DNA/RNA binding conditions (e.g., condi-tions in a cell-free system) are known in the art (see, e.g., Sambrook, et al., Molecular Cloning: A Laboratory Manual, Cold Spring Harbor Laboratory Press). The strand of the target DNA that is complementary to and hybridizes with the guide RNA is referred to as the "complementary strand" and the strand of the target DNA that is complementary to the "complementary strand" (and is therefore not complemen-tary to the guide RNA) is referred to as the "noncomple-mentary strand" or "non-complementary strand." By "site-directed modifying polypeptide" or "RNA-binding site-directed polypeptide" or "RNA-binding site-directed modifying polypeptide" or "site-directed polypeptide" it is meant a polypeptide that binds RNA and is targeted to a specific DNA sequence. A site-directed modifying polypep-tide as described herein is targeted to a specific DNA sequence by the RNA molecule to which it is bound. The RNA molecule comprises a sequence that binds, hybridizes to, or is complementary to a target sequence within the target DNA, thus targeting the bound polypeptide to a specific location within the target DNA (the target sequence).

As used herein, "transgene" means non-native genetic material that, upon introduction to a recipient cell, has the potential to change the recipient cell's phenotype.

As used herein, "upstream" or means a genetic locus or sequence position that is located closer the 5'-terminus in relation to the reference locus, wherein the oligonucleotide sequence begins with the 5'-terminus and runs "5' to 3'" until ending at the 3'-terminus.

The following examples are provided to illustrate various embodiments of the present invention. The examples are illustrative and are not intended to limit the invention in any way.

Example 1

Materials and Methods

Plasmid construction: A CRISPR recognition site was identified within exon 1 of the mouse Cypor gene using an online design tool (available at www.crispr.mit.edu) having the sequence 5'-TCGTGGGGGTCCTGACCTAC-3' (SEQ ID NO: 518). Oligonucleotides encoding this sequence were annealed and ligated into pX330 (Addgene cat. 42230; Watertown, MA) cut with BbsI. pX330 is a human codon-optimized SpCas9 and chimeric guide RNA expression plasmid (Cong, et al. Science (2013) 339(6121):819-23). Briefly, the plasmid comprises the gRNA under control of the U6 promoter and SpCas9 under the control of the CBh promoter (a hybrid chicken beta actin promoter). The oli-gonucleotide sequences were 5'-CACCGTCGTGGGGGTCCTGACCTAC-3' (SEQ ID NO: 519) and 5'-AAACGTAGGTCAGGACCCC-CACGAC-3' (SEQ ID NO: 520). The resulting plasmid (pX330-Cypor) was validated to cut the targeted sequence using the Guide-It™ Mutation Detection kit (Takara Bio USA, Inc., Mountain View, CA).

Animal procedures: Male 129/sv mice, 7-9 weeks of age, were administered 40 µg of the pX330-Cypor plasmid diluted in saline by hydrodynamic tail vein injection. After three weeks, the mice were divided into two cohorts: four mice were given twice weekly injections of acetaminophen (APAP, 13 mg/ml in saline) by IP injection, 16 injections total. Three mice were reserved as controls and did not receive APAP. For the final 6 APAP doses, the mice were fasted 16 hours prior to injection. Alanine transaminase (ALT) levels were measured 6-20 hours following APAP injection from 10 μl of blood drawn from a saphenous vein puncture using the ALT Reagent Kit (available at BKKits-.com, BQ 004A-CR). Mice were sacrificed two weeks after the final APAP injection and the livers were harvested.

Immunofluorescence: Liver sections were fixed in paraformaldehyde for 5 hours, cryoprotected in 30% sucrose overnight, and embedded in optimal cutting temperature (OCT) compound. Seven-micro sections were washed in PBS, permeabilized 12 minutes in phosphate-buffered saline (PBS) with 0.1% Triton X-100, blocked with 0.3 M glycine for 30 minutes, and incubated with primary antibody overnight at 4° C. (Abcam ab180597 (Cambridge, United Kingdom); 1:200 in PBS with 10% normal goat serum). After washing 3×5 minutes in PBS, sections were incubated in secondary antibody (Goat anti-Rabbit Alexa Fluor® 555, Invitrogen cat. A27039 (Carlsbad, CA), diluted 1/2000) for 1 hour at room temperature. Sections were mounted in DAPI Fluoromount-G® (Southern Biotech, Inc., Birmingham, AL) and visualized using a Zeiss confocal microscope.

Results

Figure 2:
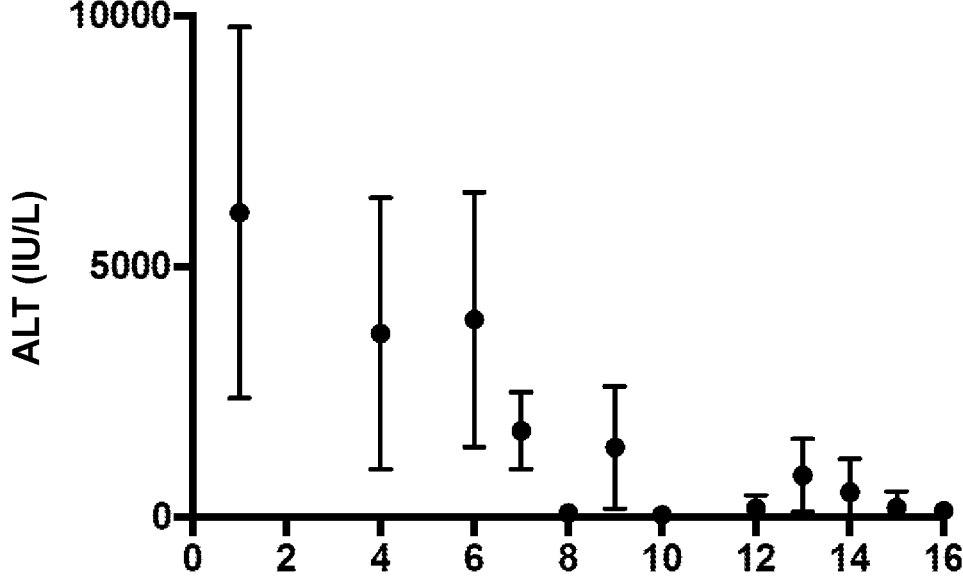
FIG. 2 provides a graph of blood alanine aminotransferase (ALT) levels, an indicator of liver damage, over time in mice injected with pX330-Cypor and treated with acetaminophen.
Figure 3:
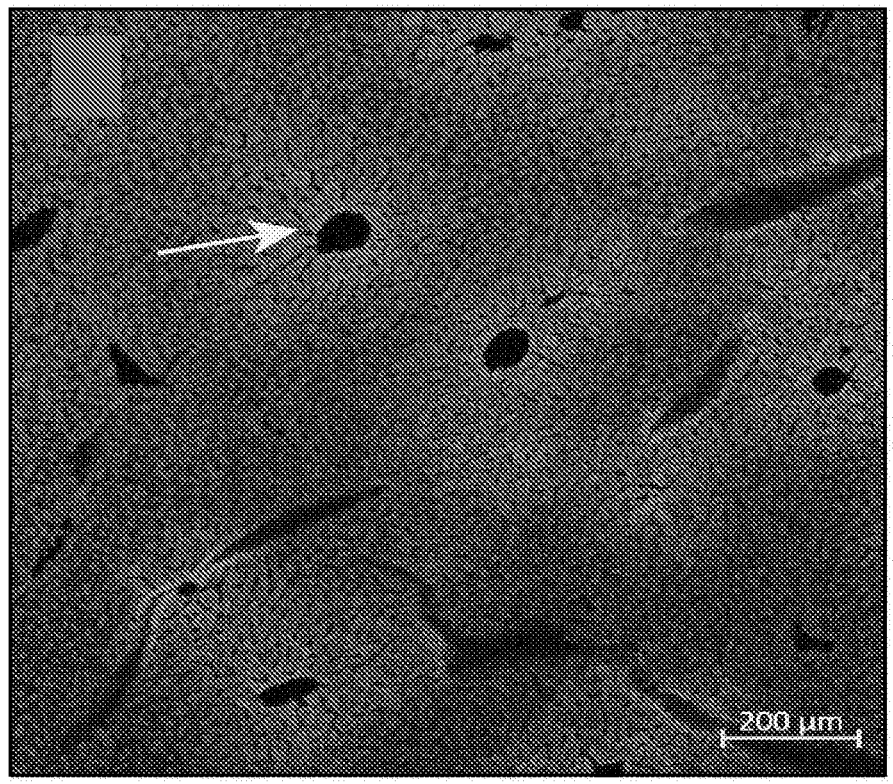
FIG. 3 provides CYPOR immunohistochemistry images of liver samples from mice transduced with pX330-Cypor that were either untreated (top image) or treated with acetaminophen (bottom image). Dashed line outlines CYPOR null nodules.
Figure 3:
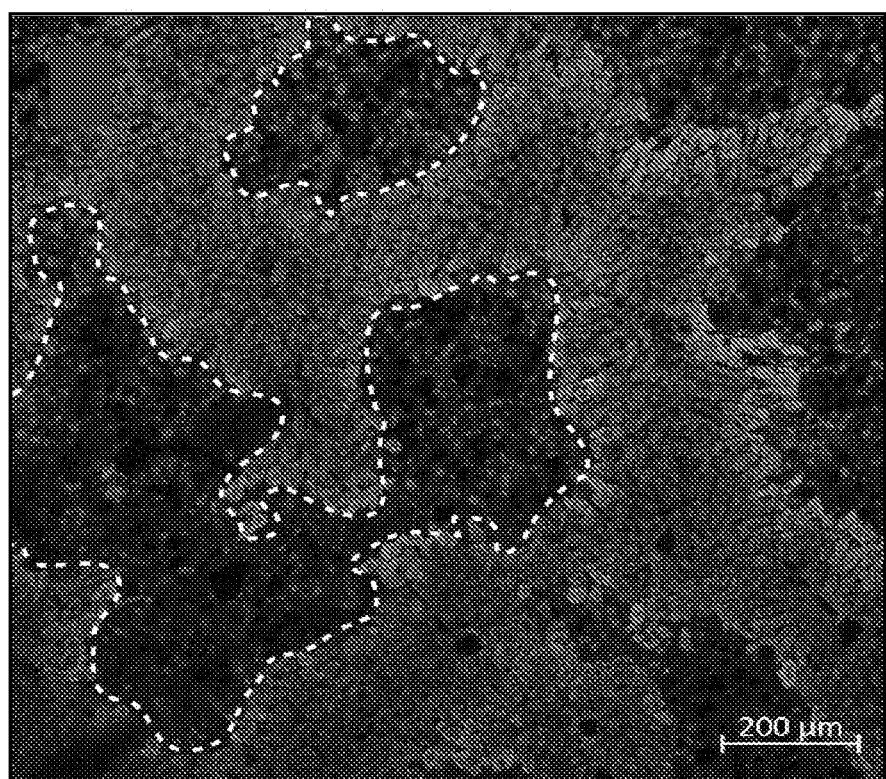

As seen in FIG. 2, liver damage as measured by blood ALT levels decreased over time for the mice injected with pX330-Cypor. The treated mice were APAP resistant after ~10 weeks. CYPOR immunohistochemistry results are provided in FIG. 3. In pX330-Cypor treated mice that received APAP injections, distribution with large CYPOR-negative nodules are present, thereby indicating clonal expansion of Cypor-null hepatocytes (bottom image; dashed line outlines Cypor null nodules). The large CYPOR-negative nodules are not present in mice not treated with APAP (top image).

Figure 4:
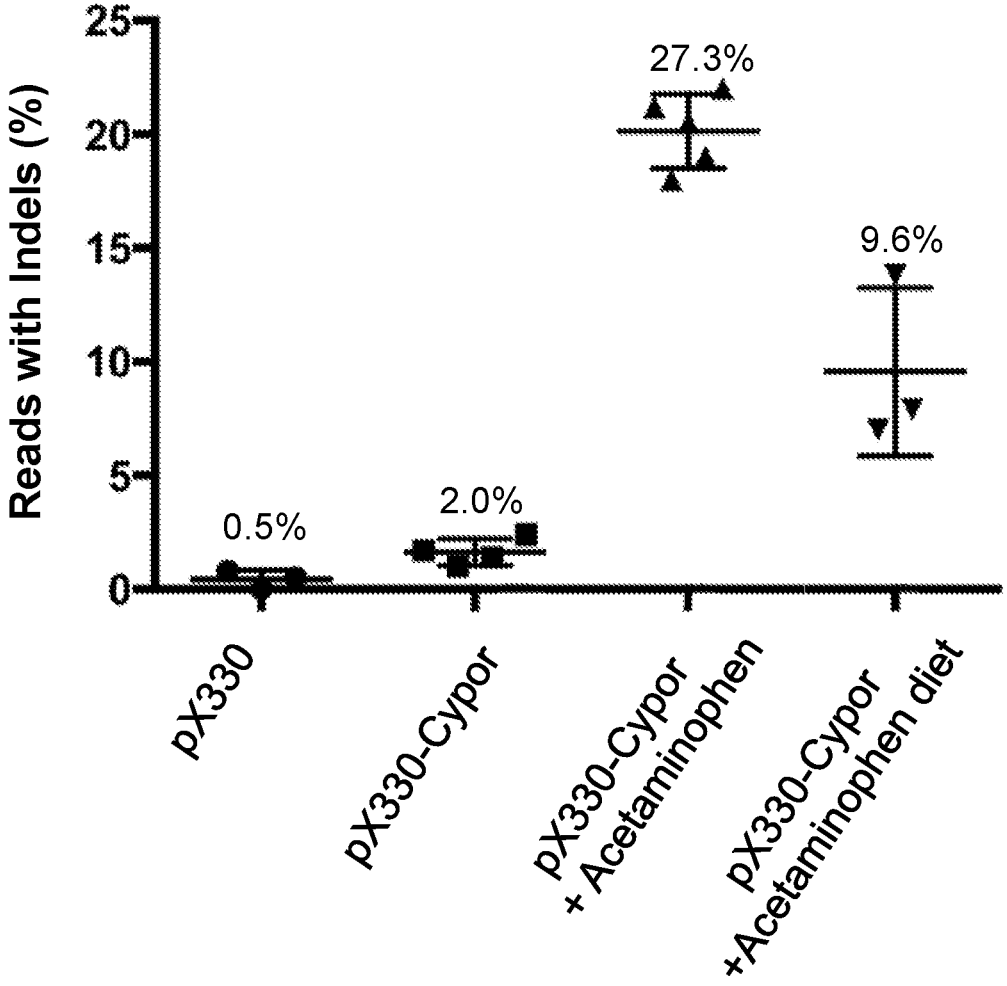
FIG. 4 provides a graph of the percentage of indels in mice injected with a control plasmid (pX330), pX330-Cypor without acetaminophen selection, pX330-Cypor with acetaminophen injections, and pX330-Cypor with an acetaminophen diet.

FIG. 4 shows the number of Cypor indels in mice injected with (from left to right) a control plasmid (pX330), pX330-Cypor without APAP selection, pX330-Cypor with APAP injections, and pX330-Cypor with an APAP diet. Indel frequency in APAP treated mice was significantly higher (p<0.01) in mice receiving APAP, either by injection or diet, thereby demonstrating selection of hepatocytes with the Cypor knockout.

Figure 5:
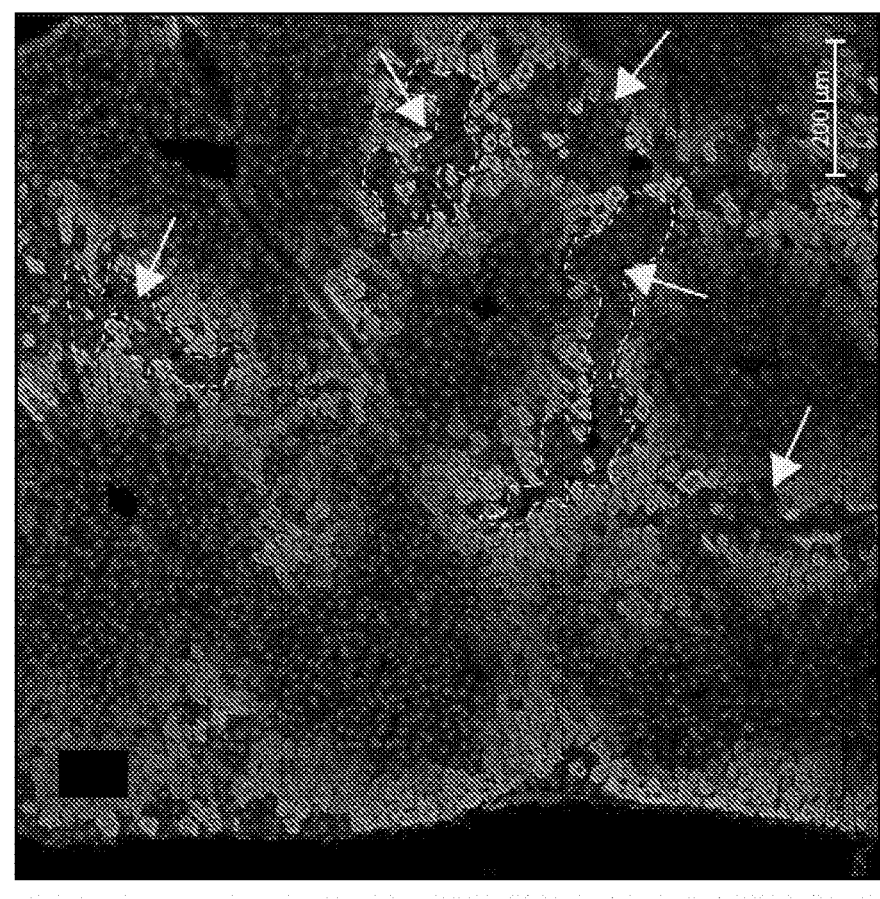
FIG. 5 provides immunohistochemistry images of liver samples from mice injected with a Cyp1A2/2E1 CRISPR knockout plasmid that were either untreated (left image) or treated with acetaminophen (right image). Arrows indicate Cyp2E1 null nodules.
Figure 5:
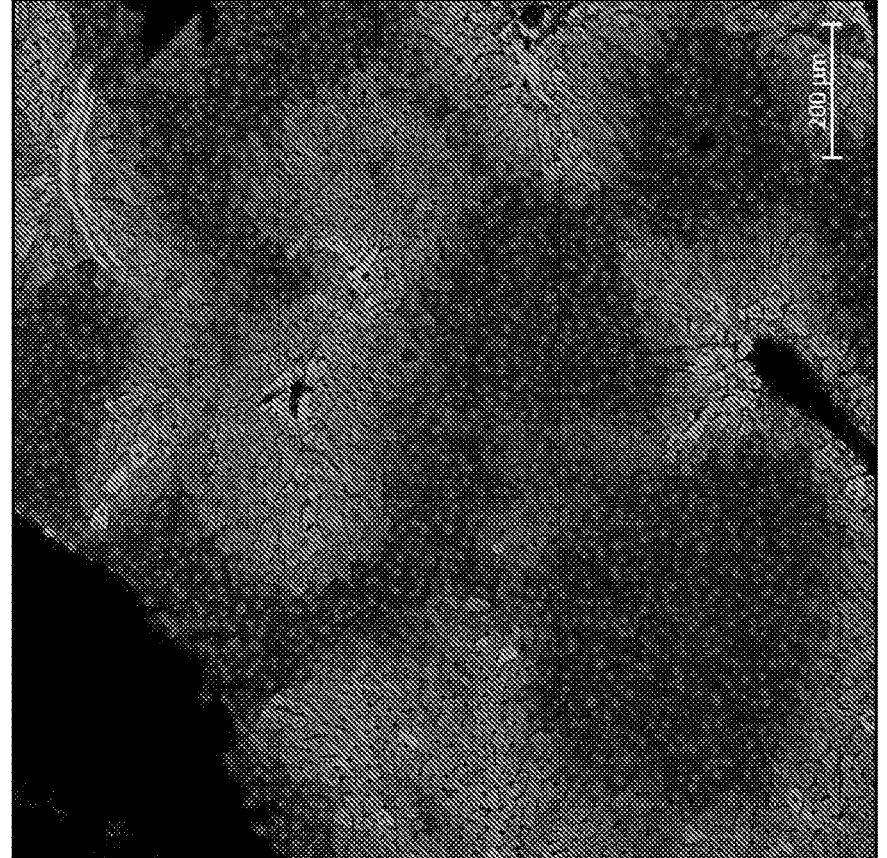

In addition to the above, mice were also injected with a Cyp1A2/2E1 CRISPR knockout plasmid and treated with APAP. As seen in FIG. 5, APAP selected liver of mice injected with the Cyp1A2/2E1 CRISPR knockout plasmid resulted in Cyp2E1 negative nodules (right image; dashed line outlines Cyp2E1 null nodules) compared to mice without APAP treatment (left image). With APAP administration the frequency of Cyp1A2 and Cyp2E1 indels increased from 1 to 12% (~17% of hepatocytes). This demonstrates that knockout of Cyp1A2 and Cyp2E1 is sufficient to achieve APAP resistance, even in Cypor proficient livers.

Example 2

The Sleeping Beauty transposon system was used to test CYPOR knockdown by shRNA. Briefly, mice were injected with two separate plasmids. One plasmid contained sleeping beauty transposase under the control of the CMV promoter. The second plasmid contained transposon cassette comprising a GFP expression cassette and U6 driven Cypor shRNA. After treatment, injected mice were exposed to 3 months of APAP selection.

Figure 6:
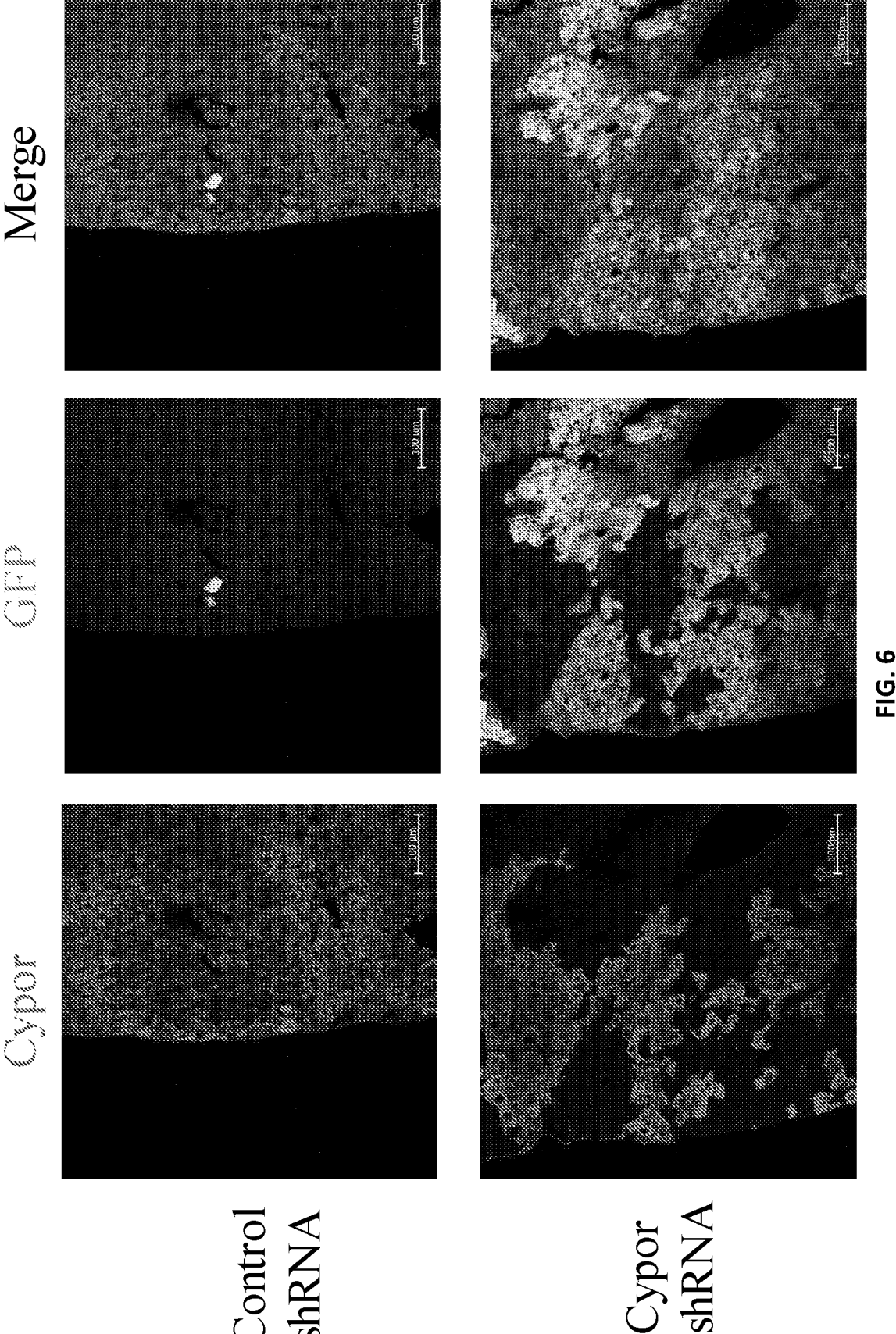
FIG. 6 provides CYPOR immunohistochemistry and fluorescence imaging of liver samples from mice transduced with GFP transposons bearing either a control shRNA (top panels) or a Cypor shRNA (bottom panels) and treated with acetaminophen.

FIG. 6 provides CYPOR immunohistochemistry and GFP fluorescence on livers from mice in the experiments treated with the Sleeping Beauty transposon system and APAP. The top panels show results from a negative control (irrelevant shRNA). Rare GFP+ cells can be seen, but no nodules have formed. The bottom panels show images from a APAP treated mice that were injected with the GFP-Cypor shRNA transposon. Large confluent areas of GFP expression are seen in Cypor negative regions. This provides clear evidence for the expansion of transposon positive hepatocytes.

Example 3

Figure 7:
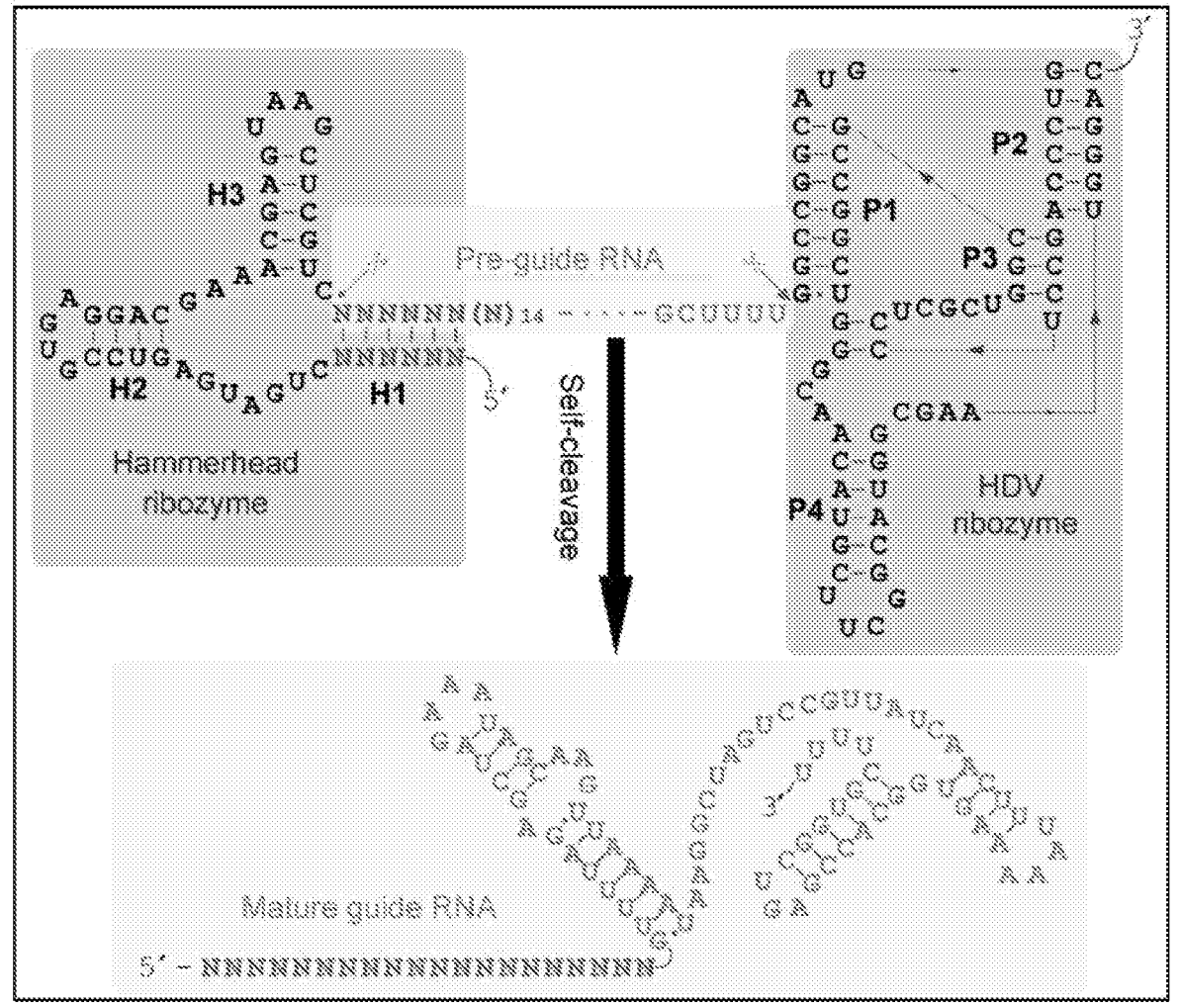
FIG. 7 provides a schematic of a self-cleaving guide RNA. Hammerhead ribozyme is SEQ ID NO: 521. HDV ribozyme is SEQ ID NO: 522. Mature gRNA is SEQ ID NO: 523.

Self-cleaving guide RNAs were also tested. Self-cleaving guide RNAs comprise ribozymes on either side of the guide RNA so that the guide RNA may be driven from a pol II promoter. For example, a hammerhead (HH) ribozyme may be at the 5' of the guide RNA and a Hepatitis delta virus (HDV) ribozyme may be at the 3' end of the guide RNA. FIG. 7 provides a schematic of the self-cleaving guide RNA.

In one experiment, a scgRNA comprising a guide RNA flanked by a hammerhead type ribozyme and a hepatitis delta virus type ribozyme was used. The targeting vector utilized for these experiments contains human Factor IX as a biomarker and the scgRNA between arms of homology to the murine albumin locus. The albumin gene was selected as an example of a cell-type specific gene locus. Vectors were designed to contain scgRNA targeting either exon 3 of 4-OH phenylpyruvate dioxygenase (Hpd), exon 4 of Hpd or exon 4 of homogentisic acid dioxygenase (Hgd). Briefly, the vector comprised, in order: left arm of homology (albumin)-p2A (2A peptide)-human Factor IX gene-region of homology (albumin)-HH ribozyme-gRNA-HDV ribozyme-right arm of homology (albumin). The homology arms allow for targeted integration (homologous recombination) and the scgRNA was embedded within an intron. Recombinant adeno-associated virus serotype 8 was generated from these vectors. Neonatal fumarylacetoacetate hydrolase knockout (Fah$^{-/-}$) mice were given rAAV8 containing the scgRNA Gene Ride vector with 1 of the 3 gRNAs followed by rAAV8 containing SpCas9 driven by the tiny liver specific promoter approximately 4 weeks later. Mice were cycled on 2-(2-nitro-4-trifluoromethylbenzoyl)-1,3-cyclohexanedione (NTBC) to allow selection of hepatocytes that have the correct integration of the targeting vector and hence express gRNAs capable of disrupting selectable genes. In Fah$^{-/-}$ mice, loss of Hpd or Hgd confers a selective growth advantage in hepatocytes. Levels of circulating human Factor IX were assessed at 5, 9, 14 and 18 weeks of age. At 5 and 9 weeks, all mice displayed low levels of human Factor IX. At 14 weeks, mice that had received the scgRNA vector with a gRNA against exon 3 of Hpd began to show increased levels of hF9. These levels significantly increased by 18 weeks of age demonstrating selection for the correctly targeted hepatocytes. Furthermore, mice that received the scgRNA vector with a gRNA targeting exon 4 of Hpd or Hgd showed high levels of hF9 by 18 weeks of age. This finding clearly demonstrates that self-cleaving ribozymes indeed can produce functional gRNAs from a pol 2 promoter and can be used to create selectable gene editing events in the liver in vivo.

The albumin locus was targeted with a GeneRide™ vector incorporating self-cleaving guide RNA against Cypor. In initial experiments, the transgene luciferase was utilized.

Briefly, the vector comprised, in order: left arm of homology-p2A (2A peptide)-luciferase gene-region of homology-HH ribozyme-gRNA-HDV ribozyme-right arm of homology. After homologous recombination into the target locus (albumin) the transgene and the self-cleaving guide RNA are expressed.

Figure 8:
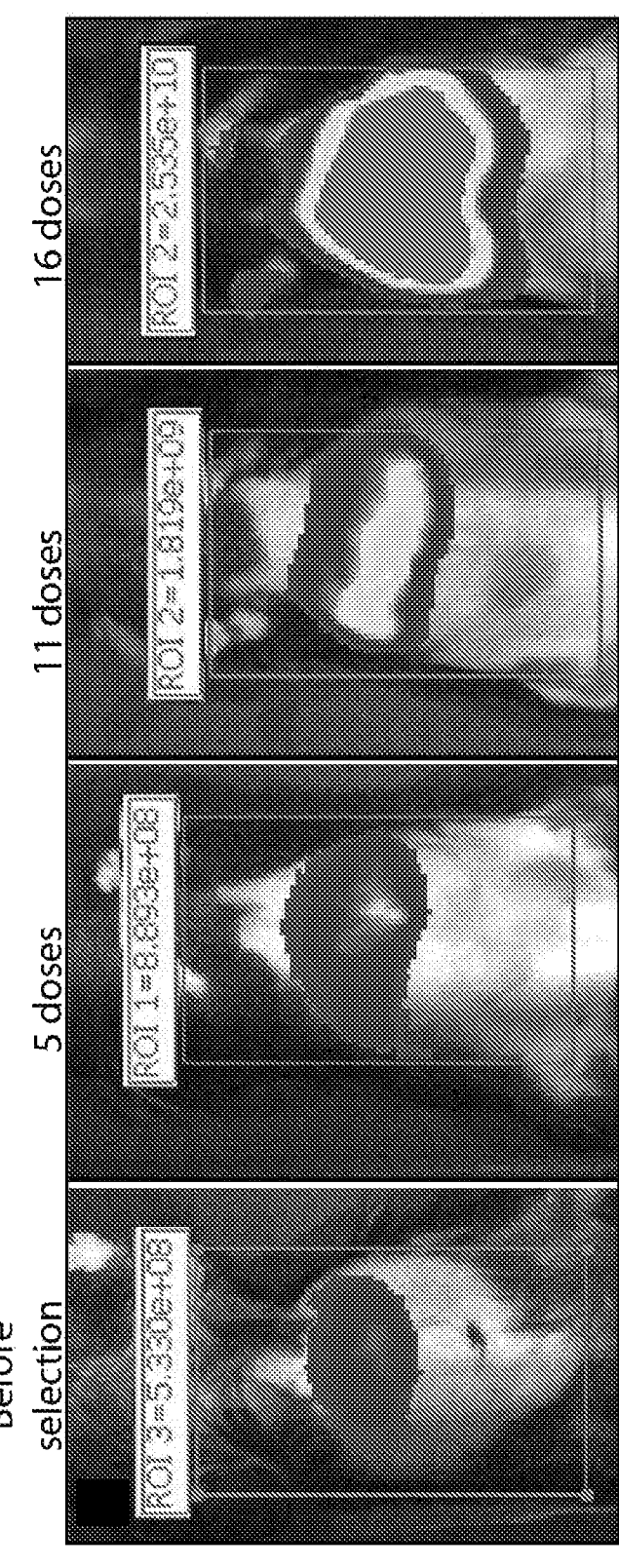
FIG. 8 provides luciferase images of livers of neonatal mice injected with a vector comprising luciferase and a self-cleaving guide RNA against Cypor and injected with cas9 at weaning, followed by acetaminophen injections for 8 weeks. Live luciferase imaging was performed on the same mouse at baseline and after 5, 11, and 16 doses.

Neonatal mice were injected with this vector and cas9 was given at weaning, followed by APAP injections for 8 weeks. Live luciferase imaging was done on the same mouse at baseline and after 5, 11 and 16 doses. Luciferase expression increased with each dose, reaching a 50× increase (see FIG. 8). At harvest, Cypor staining revealed large negative areas and indel frequency was 21%.

Figure 9:
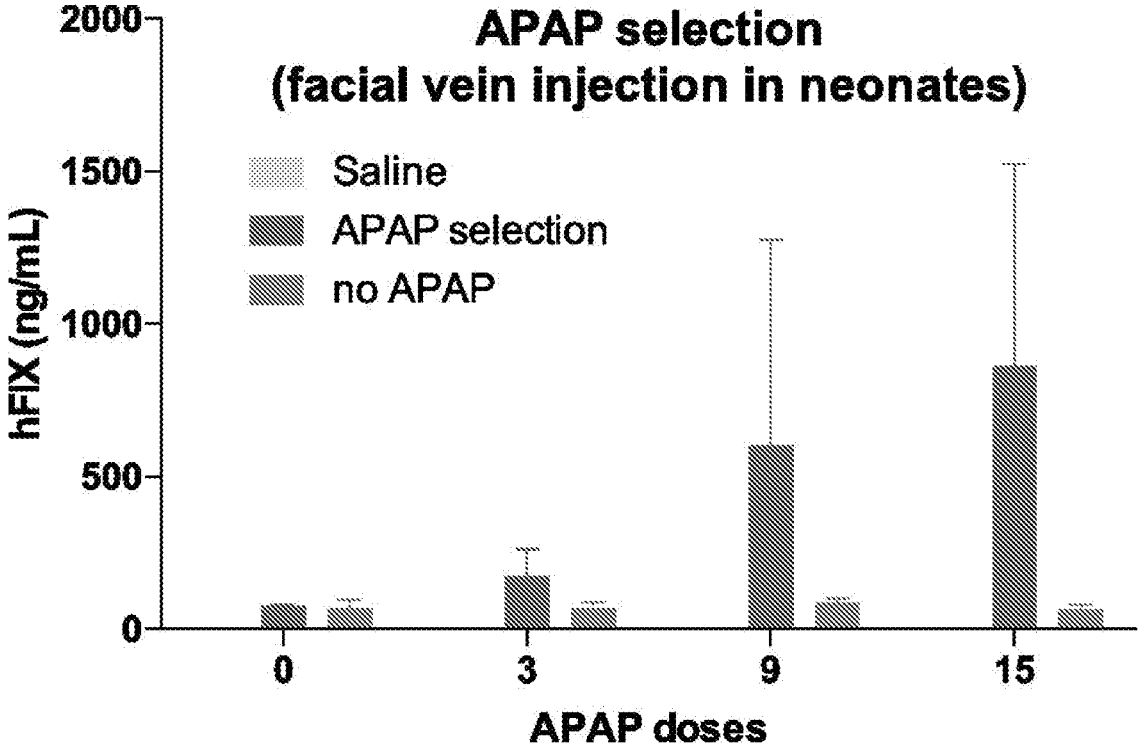
FIG. 9 provides a graph of human Factor IX levels in the blood of mice injected with saline or with AAV GRCyporF9 as neonates and given a single dose of Cas9 at weaning. Mice were then either untreated or treated with acetaminophen twice weekly. Human Factor IX levels were measured after 0, 3, 9 and 15 doses of acetaminophen.

In additional experiments, human Factor IX was expressed as the transgene in the above vector instead of luciferase. The vector was named GRCyporF9. Neonates were injected with AAV GRCyporF9 as neonates and given a single dose of Cas9 at weaning. They were then injected with APAP twice weekly. FIG. 9 shows the human Factor IX levels in blood after 0, 3, 9 and 15 doses of APAP. There was a clear increase in human Factor IX levels in response to the APAP injections. GRCyporF9 injected mice that did not receive APAP, showed no increases and saline controls were also negative.

Figure 10:
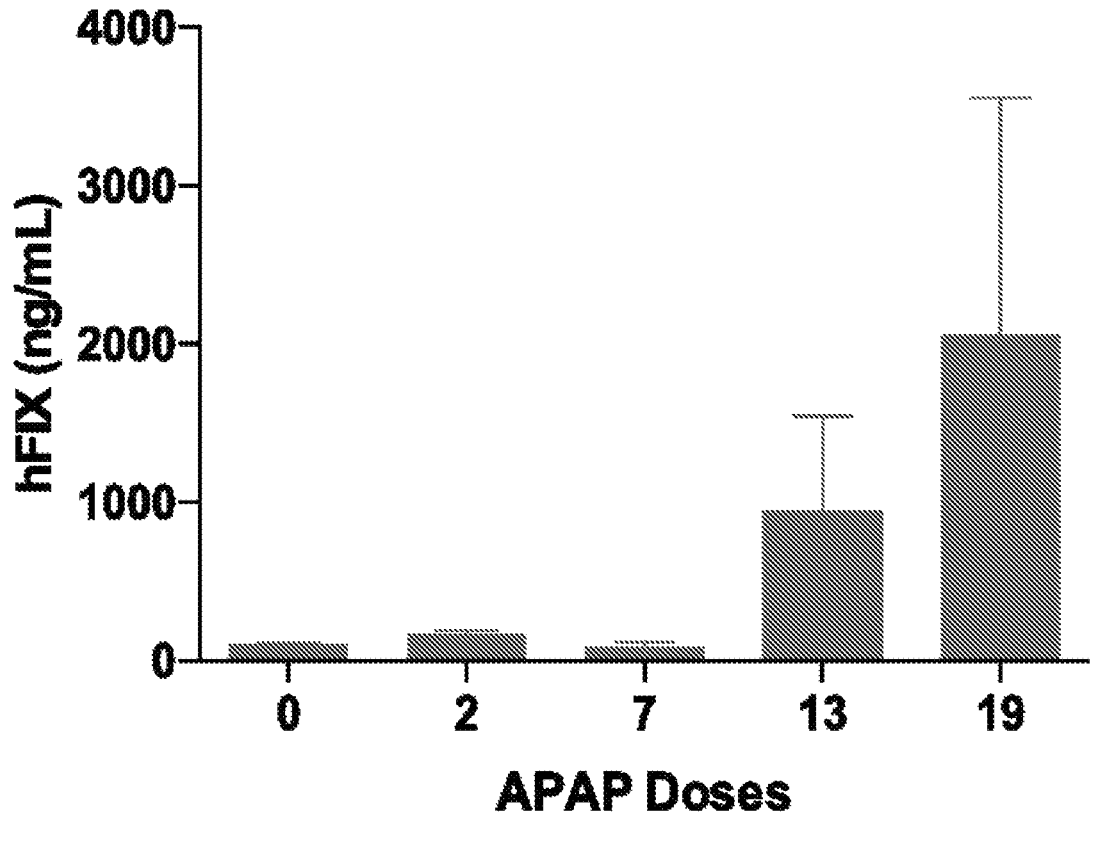
FIG. 10 provides a graph of human Factor IX levels in the blood of adult mice injected with AAV GRCyporF9 and treated with acetaminophen. Human Factor IX levels were determined after 0, 2, 7, 13 and 19 doses.

AAV GRCyporF9 was also injected into adult mice along with Cas9. The mice were subsequently given multiple doses of APAP. Human Factor IX levels after 0, 2, 7, 13 and 19 doses are shown in FIG. 10 with clear APAP dependent increases. Mice were killed after 19 doses and the Cypor indel frequency in hepatocytes was measured. All APAP selected mice had indel frequencies of ~20% indicating significant selection.

Figure 11:
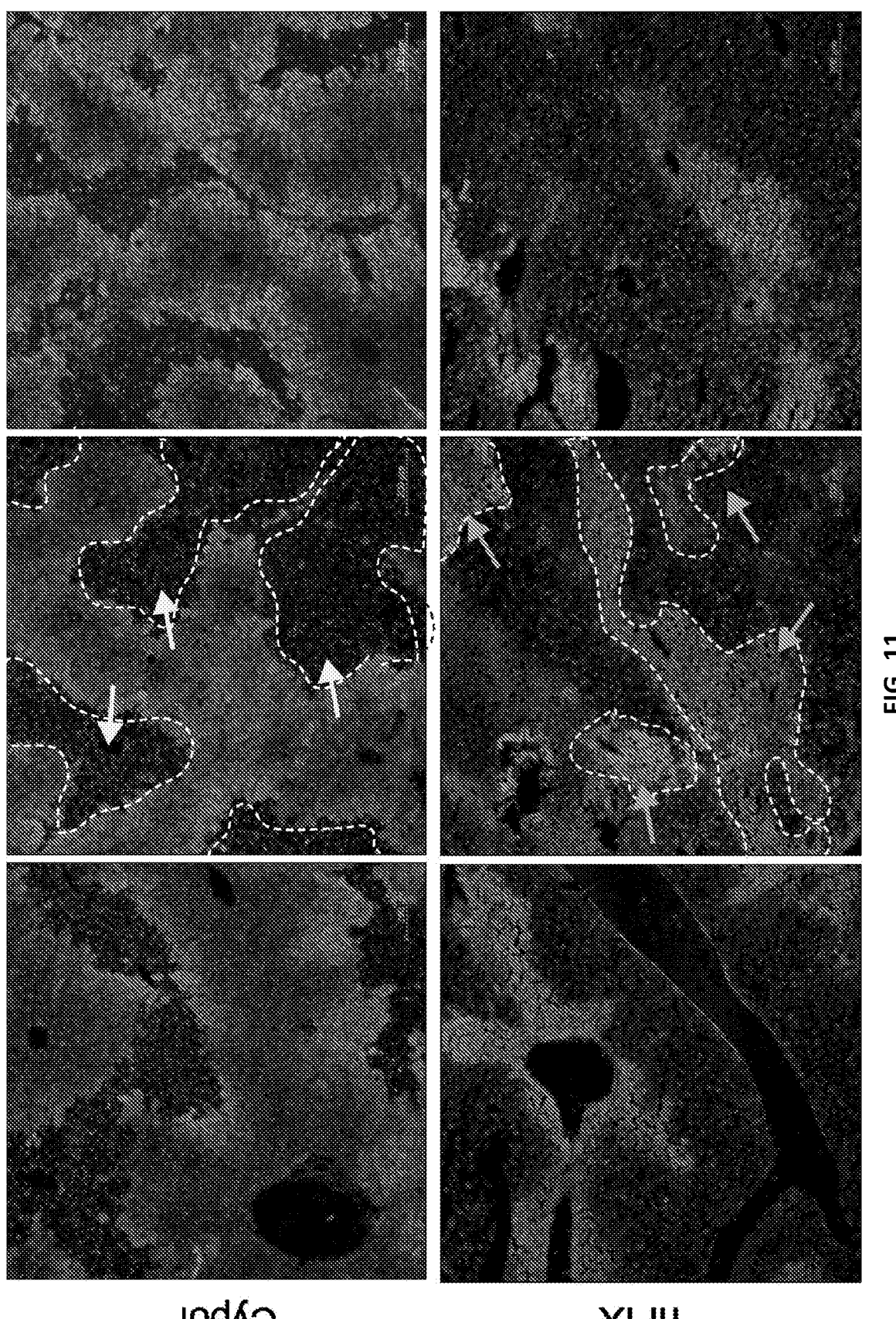
FIG. 11 provides images of CYPOR (top panels) and human Factor IX (bottom panels) immunohistochemistry of tissue samples from GRCyporF9 treated mice after acetaminophen treatment. In top panels, CYPOR negative tissue is indicated by dotted line and arrows. In bottom panels, mouse hepatocytes positive for human Factor IX are indicated by dotted line and arrows.

FIG. 11 shows CYPOR (top panels) and human Factor IX (bottom panels) immunohistochemistry in GRCyporF9 treated mice after APAP selection. 3 mice are shown. All APAP treated mice showed extensive areas of Cypor negativity around the central vein (dotted line and arrows in middle panel). The same animals showed large areas of human Factor IX positive mouse hepatocytes in the same distribution pattern (dotted line and arrows in the middle panel). These data show that selected Cypor negative hepatocytes express the therapeutic transgene.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for selectively amplifying and/or expanding a population of hepatocytes in a subject, the method comprising the steps of:
   a) inhibiting a cytochrome p450 reductase (POR) in a hepatocyte; and
   b) administering a protoxin to a subject having a hepatocyte produced by step a), wherein the protoxin is a small molecule,
   wherein step a) comprises i) administering an inhibitory nucleic acid molecule or a nucleic acid molecule encoding the inhibitory nucleic acid molecule to the hepatocyte or subject, wherein said inhibitory nucleic acid molecule is specific for POR; or ii) administering Cas9 and a guide RNA (gRNA) specific for the POR gene or a nucleic acid molecule encoding the gRNA to the hepatocyte or subject, wherein said gRNA sequence combines with said Cas9 resulting in cleavage of said POR gene,
   wherein said protoxin is metabolized into a toxin in hepatocytes not produced by step a) in said subject and induces cell death, and
   wherein said protoxin is not converted to a toxic metabolite in hepatocytes produced by step a), thereby allowing for amplification and/or expansion of the hepatocytes within said subject.

2. The method of claim 1, further comprising introducing a transgene into the hepatocyte prior to step b).

3. The method of claim 1, wherein step a) is performed in vitro and the hepatocytes are administered to the subject before step b).

4. The method of claim 1, wherein step a) is performed in vivo.

5. The method of claim 1, wherein step a) comprises administering an inhibitory nucleic acid molecule or a nucleic acid molecule encoding the inhibitory nucleic acid molecule to the hepatocyte or subject, wherein said inhibitory nucleic acid molecule is specific for POR.

6. The method of claim 5, wherein said inhibitory nucleic acid molecule is an shRNA.

7. The method of claim 5, wherein step a) comprises administering a vector comprising a nucleic acid molecule encoding the inhibitory nucleic acid molecule and a transgene to said hepatocyte or subject.

8. The method of claim 7, wherein said vector is a viral vector.

9. The method of claim 8, wherein said viral vector is an AAV vector.

10. The method of claim 7, wherein said vector is an integrating vector.

11. The method of claim 10, wherein said integrating vector lacks promoters.

12. The method of claim 1, wherein step a) comprises administering Cas9 and a guide RNA (gRNA) specific for the POR gene or a nucleic acid molecule encoding the gRNA to the hepatocyte or subject, wherein said gRNA sequence combines with said Cas9 resulting in cleavage of said POR gene.

13. The method of claim 12, wherein said gRNA is a self-cleaving guide RNA (scgRNA), wherein said scgRNA comprises a gRNA flanked by a self-cleaving ribozyme at both the 5' and 3' ends.

14. The method of claim 13, wherein said scgRNA is expressed from an RNA polymerase II promoter.

15. The method of claim 12, wherein step a) comprises administering a vector comprising a nucleic acid molecule encoding the gRNA and a transgene to said hepatocyte or subject.

16. The method of claim 15, wherein said vector is a viral vector.

17. The method of claim 16, wherein said viral vector is an AAV vector.

18. The method of claim 15, wherein said vector is an integrating vector.

19. The method of claim 18, wherein said integrating vector lacks promoters.

20. The method of claim 1, wherein said protoxin is administered in an amount sufficient to result in mild hepatotoxicity in the subject, wherein said mild hepatoxicity is characterized by i) raised serum aminotransferase or alkaline phosphatase levels or both, and ii) a total serum bilirubin less than 2.5 mg/dL, and coagulopathy with an international normalized ratio (INR)<1.5.

21. The method of claim 1, wherein said protoxin is administered in an amount sufficient to result in moderate hepatotoxicity in the subject, wherein said moderate hepatotoxicity is characterized by i) raised serum aminotransferase or alkaline phosphatase levels or both, and ii) a total serum bilirubin level of greater than or equal to 2.5 mg/dL or coagulopathy with an international normalized ratio (INR) ≥1.5 without hyperbilirubinemia.

22. The method of claim 1, wherein said protoxin is administered in an amount sufficient to elevate in the subject's levels of at least one liver enzyme selected from the group comprising alanine aminotransferase, aspartate transaminase, alkaline phosphatase, and gamma-glutamyl transpeptidase.

23. The method of claim 1, wherein said protoxin is selected from the group consisting of acetaminophen, retrorsine, cyclophosphamide, tamoxifen, ketoconazole, tramadol, tacrine, lasiocarpine, senkirkin, dacarbazine, methoxymorpholinyl doxorubicin (PNU 152243), ifosfamide, trofosfamide, pradefovir, MB07133, buparvaquone hydroxylamine, nabumetone hydroxyimine, DB289, furamidine, sibrafibin, ximelagatran, guanoxabenz, AQ4N, 4-ipomeanol, clopidogrel, V-PYRRO/NO, V-PROLI/NO, and tegafur.

24. The method of claim 1, wherein the protoxin is acetaminophen.

25. The method of claim 24, wherein the acetaminophen is administered to the subject at a dose of 6 grams per day on consecutive days.

26. The method of claim 24, wherein the acetaminophen is administered to the subject at a single dose of 10 grams.

27. A method for selectively amplifying and/or expanding a population of hepatocytes in a subject, the method consisting of the steps of:
   a) inhibiting cytochrome p450 reductase (POR) in a hepatocyte and optionally introducing a transgene into the hepatocyte; and
   b) administering acetaminophen to a subject having a hepatocyte produced by step a),
   wherein step a) consists of i) administering an inhibitory nucleic acid molecule or a nucleic acid molecule encoding the inhibitory nucleic acid molecule to the hepatocyte or subject, wherein said inhibitory nucleic acid molecule is specific for POR; or ii) administering Cas9 and a guide RNA (gRNA) specific for the POR gene or a nucleic acid molecule encoding the gRNA to the hepatocyte or subject, wherein said gRNA sequence combines with said Cas9 resulting in cleavage of said POR gene; and
   wherein said acetaminophen is not converted to a toxic metabolite in hepatocytes produced by step a), thereby allowing for amplification and/or expansion of the hepatocytes within said subject.

28. The method of claim 27, wherein a transgene is inserted into the hepatocyte prior to step b).

29. The method of claim 27, wherein said inhibitory nucleic acid molecule is an shRNA.

30. The method of claim 27, wherein said nucleic acid molecule encoding the inhibitory nucleic acid is a vector.

31. The method of claim 30, wherein said vector is a viral vector.

32. The method of claim 31, wherein said viral vector is an AAV vector.

33. The method of claim 30, wherein said vector is an integrating vector.

34. The method of claim 33, wherein said integrating vector lacks promoters.

35. The method of claim 27, wherein said gRNA is a self-cleaving guide RNA (scgRNA), wherein said scgRNA consists of a gRNA flanked by a self-cleaving ribozyme at both the 5' and 3' ends.

36. The method of claim 35, wherein said scgRNA is expressed from an RNA polymerase II promoter.

37. The method of claim 27, wherein the nucleic acid molecule encoding the gRNA is a vector.

38. The method of claim 37, wherein said vector is a viral vector.

39. The method of claim 38, wherein said viral vector is an AAV vector.

40. The method of claim 37, wherein said vector is an integrating vector.

41. The method of claim 40, wherein said integrating vector lacks promoters.

42. The method of claim 27, wherein said acetaminophen is administered in an amount sufficient to result in mild hepatotoxicity in the subject, wherein said mild hepatotoxicity is characterized by i) raised serum aminotransferase or alkaline phosphatase levels or both, and ii) a total serum bilirubin less than 2.5 mg/dL, and coagulopathy with an international normalized ratio (INR)<1.5.

43. The method of claim 27, wherein said acetaminophen is administered in an amount sufficient to result in moderate hepatotoxicity in the subject, wherein said moderate hepatotoxicity is characterized by i) raised serum aminotransferase or alkaline phosphatase levels or both, and ii) total serum bilirubin level of greater than or equal to 2.5 mg/dL or coagulopathy with an international normalized ratio (INR) ≥1.5 without hyperbilirubinemia.

44. The method of claim 27, wherein said acetaminophen is administered in an amount sufficient to elevate in the subject's levels of at least one liver enzyme selected from the group comprising alanine aminotransferase, aspartate transaminase, alkaline phosphatase, and gamma-glutamyl transpeptidase.

45. The method of claim 27, wherein said acetaminophen is administered to the subject at a dose of 6 grams per day on consecutive days.

46. The method of claim 27, wherein said acetaminophen is administered to the subject at a single dose of 10 grams.

* * * * *